United States Patent [19]
Applegate et al.

[11] Patent Number: 5,843,766
[45] Date of Patent: Dec. 1, 1998

[54] APPARATUS FOR THE GROWTH AND PACKAGING OF THREE DIMENSIONAL TISSUE CULTURES

[75] Inventors: Dawn Orton Applegate; Mark Applegate; Mark Baumgartner; John W. Bennett; John Danssaert; Robert Hardin, all of San Diego; Lee Laiterman, Los Gatos; Fred Schramm, Del Mar; William R. Tolbert, San Diego, all of Calif.

[73] Assignee: Advanced Tissue Sciences, Inc., La Jolla, Calif.

[21] Appl. No.: 597,053

[22] Filed: Feb. 5, 1996

Related U.S. Application Data

[63] Continuation-in-part of Ser. No. 480,992, Jun. 7, 1995.

[51] Int. Cl.[6] ................................................ C12M 3/00
[52] U.S. Cl. .................... 435/284.1; 435/289.1; 435/297.2; 435/297.5; 435/299.1; 435/293.1
[58] Field of Search .............................. 435/288.1, 288.2, 435/288.3, 288.5, 289.1, 293.1, 293.2, 297.5, 298.1, 299.2, 304.1, 304.2, 305.1, 305.2, 297.1, 297.2, 1.1, 1.2, 399, 284.1; 210/321.75, 321.76, 321.84, 321.85, 456; 600/36; 623/15

[56] References Cited

U.S. PATENT DOCUMENTS

| | | | |
|---|---|---|---|
| 2,784,843 | 3/1957 | Braunlich . | |
| 3,734,851 | 5/1973 | Matsumura . | |
| 3,952,577 | 4/1976 | Hayes et al. | 73/55 |
| 4,201,845 | 5/1980 | Feder et al. | 435/285 |
| 4,417,861 | 11/1983 | Tolbert . | |
| 4,639,422 | 1/1987 | Geimer et al. . | |
| 4,681,853 | 7/1987 | Hardy et al. . | |
| 4,846,970 | 7/1989 | Bertelsen et al. . | |
| 4,944,877 | 7/1990 | Maples | 210/321.76 |
| 4,988,623 | 1/1991 | Schwarz et al. . | |
| 5,026,650 | 6/1991 | Schwarz et al. . | |
| 5,043,260 | 8/1991 | Jauregul . | |
| 5,068,195 | 11/1991 | Howell et al. | 435/284 |
| 5,081,035 | 1/1992 | Halberstadt et al. . | |
| 5,153,131 | 10/1992 | Wolf et al. . | |

(List continued on next page.)

FOREIGN PATENT DOCUMENTS

| | | |
|---|---|---|
| WO 90/13639 | 11/1990 | WIPO . |
| WO 92/11355 | 7/1992 | WIPO . |
| WO 93/01843 | 2/1993 | WIPO . |
| WO 93/12805 | 7/1993 | WIPO . |
| WO 93/18132 | 10/1993 | WIPO . |
| WO 94/25584 | 11/1994 | WIPO . |

OTHER PUBLICATIONS

Atkinson et al.; *Biochemical Engineering and Biotechnology Handbook*; pp. 476–487 (1991).

Halberstadt et al., "The In Vitro Growth of a Three–Dimensional Human Dermal Replacement Using a Single–Pass Perfusion System," *Biotechnology and Bioengineering* 43:740–746 (1994).

*Primary Examiner*—William H. Beisner

[57] ABSTRACT

A tissue culture chamber is disclosed. The chamber is a casing that provides for growth of three-dimensional tissue, and more specifically for the growth of skin tissue, that can be grown, preserved in frozen form, and shipped to the end user in the same aseptic container. The tissue culture chamber includes a casing comprising a substrate within the casing designed to facilitate three-dimensional tissue growth on the surface of the substrate. The casing includes an inlet and an outlet port which assist the inflow and outflow of media. The casing also includes at least one flow distributor. In one embodiment, the flow distributor is a baffle, which is used to distribute the flow of the media within the chamber to create a continuous, uniform piece of three-dimensional tissue. In a second embodiment, the flow distributor is a combination of deflector plates, distribution channels, and a flow channel. In each embodiment, the casing further includes a seal so as to ensure an aseptic environment inside the chamber during tissue growth and storage.

63 Claims, 21 Drawing Sheets

U.S. PATENT DOCUMENTS

| | | |
|---|---|---|
| 5,153,132 | 10/1992 | Goodwin et al. . |
| 5,153,133 | 10/1992 | Schwarz et al. . |
| 5,155,034 | 10/1992 | Wolf et al. . |
| 5,155,035 | 10/1992 | Schwarz et al. . |
| 5,230,693 | 7/1993 | Williams et al. . |
| 5,240,854 | 8/1993 | Berry et al. ............................. 435/284 |
| 5,266,480 | 11/1993 | Naughton et al. . |
| 5,308,764 | 5/1994 | Goodwin et al. . |
| 5,376,548 | 12/1994 | Matsuo et al. ......................... 435/284 |
| 5,417,576 | 5/1995 | Hill ...................................... 435/303.4 |

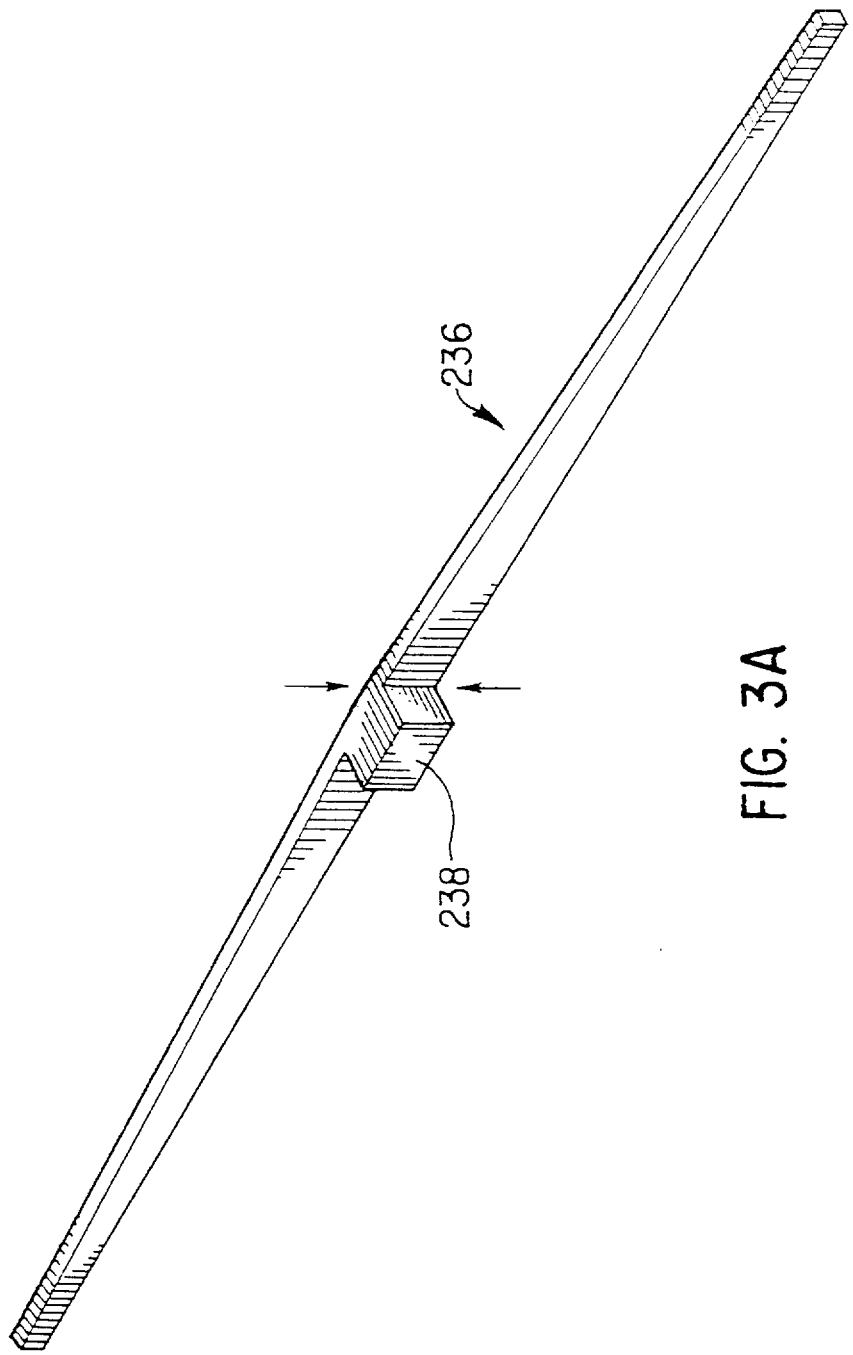

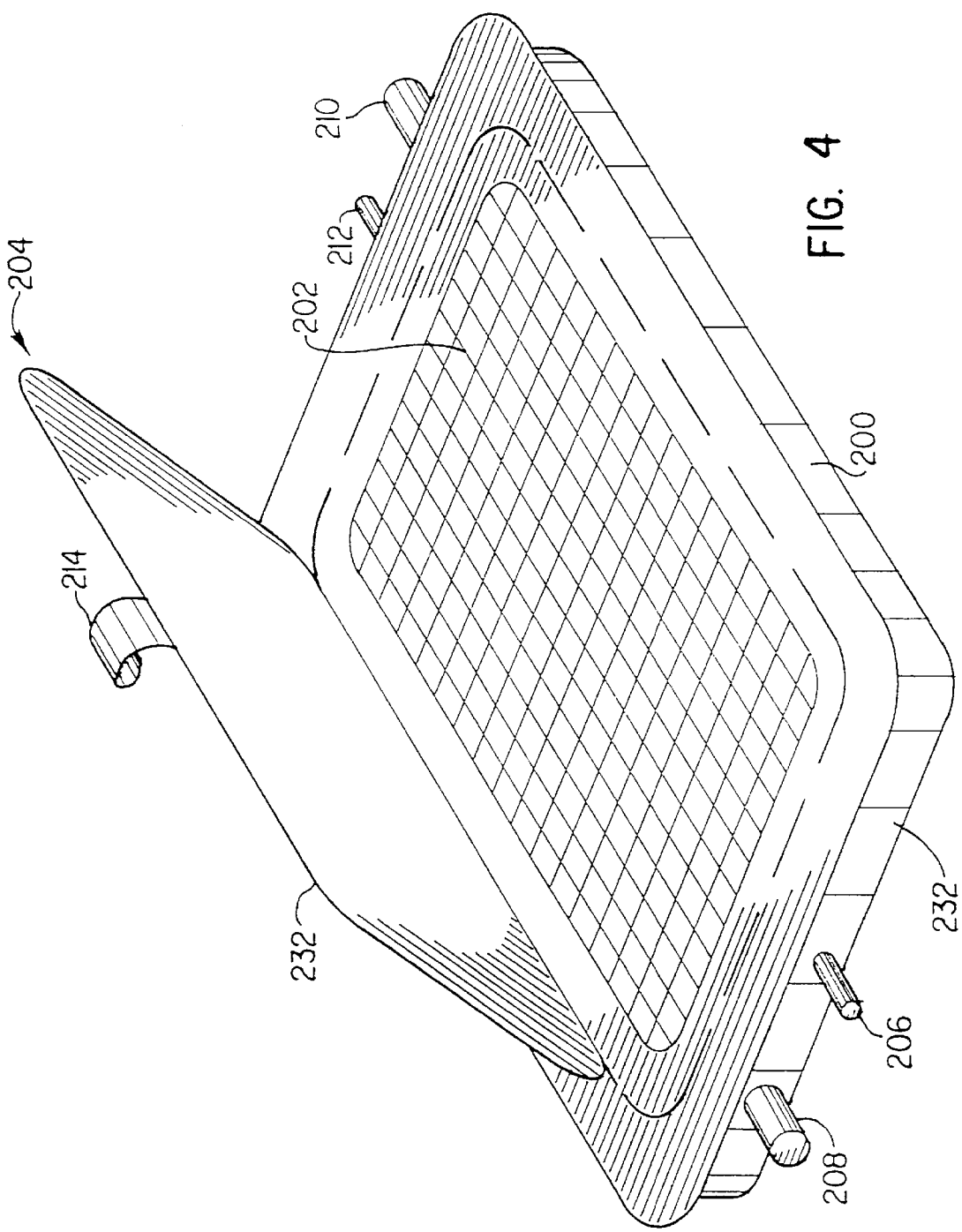

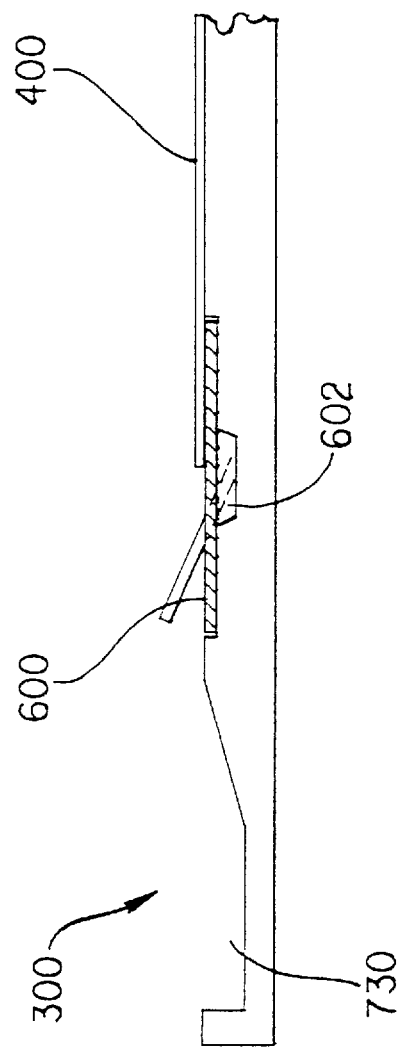

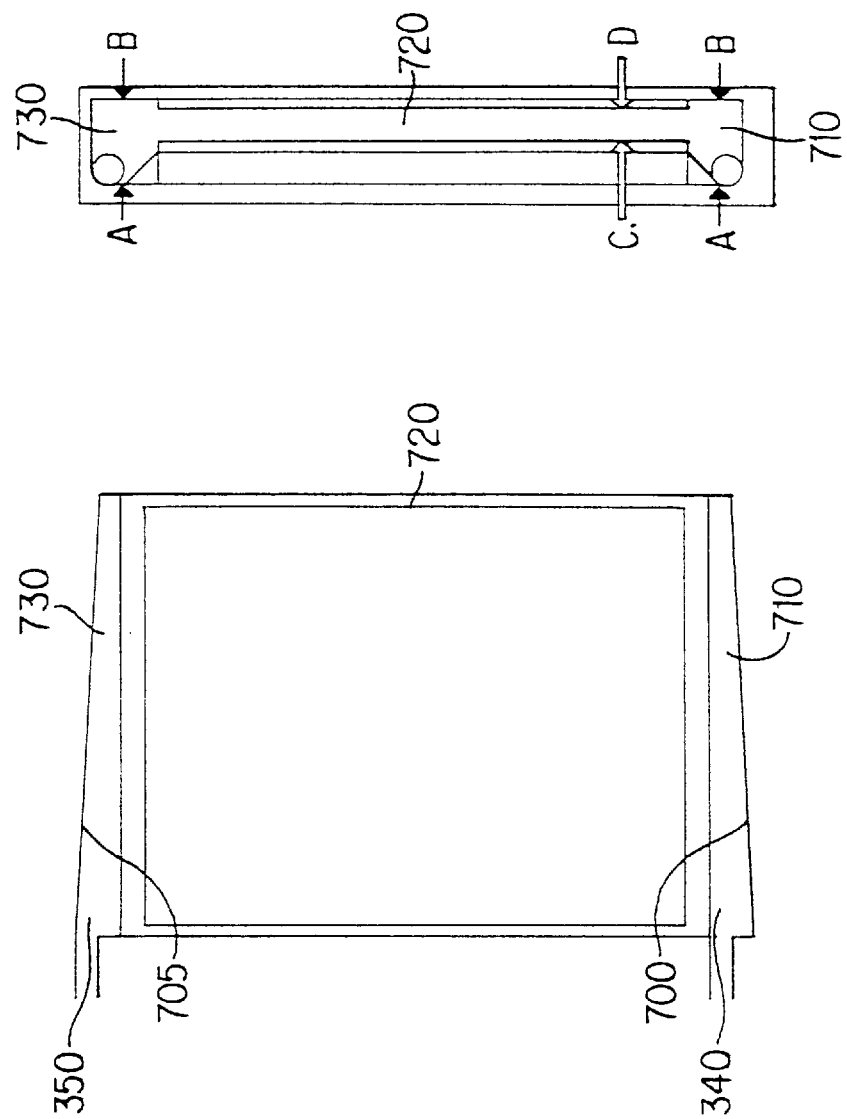

APPARATUS FOR THE GROWTH AND PACKAGING OF THREE DIMENSIONAL TISSUE CULTURES

RELATED APPLICATION

This application is a continuation-in-part of U.S. patent application Ser. No. 08/480,992 filed Jun. 7, 1995 and entitled "Chamber For Growth of Three Dimensional Tissue Cultures."

BACKGROUND OF THE INVENTION

The present invention relates to a chamber for the growth of three-dimensional tissue in general, and more specifically to the growth of skin tissue. The growth of three-dimensional tissue has recently become possible as, for example, described in U.S. Pat. No. 5,266,480 to Naughton et al. Three-dimensional tissue has a number of uses, including use of the tissue for treatment of burn victims.

Conventional means of tissue culture have been limited by the need for human supervision and control of the media flow which feeds nutrients to the cells over the time needed for the growth into tissue, which limits the amount of tissue that can be cultured at a single time. For example, in an article entitled "The In Vitro Growth of a Three-Dimensional Human Dermal Replacement Using a Single-Pass Perfusion System" 43 Biotechnology and Bioengineering 740–746 (April 1994), a closed, single pass perfusion system is disclosed in which growth medium is passed through a parallel configuration of Teflon™ bag bioreactors. Each bag bioreactor contains a biodegradable mesh on a Teflon™ frame, onto which tissue is grown. The system described only provides for 16 bag bioreactors, which must be carefully handled to avoid damaging the tissue as it grows.

SUMMARY OF THE INVENTION

The object of the present invention is to meet the need for a tissue culture chamber that will allow production of large amounts of three-dimensional tissue in a convenient form which enables aseptic processing, handling, freezing, storage, shipping, and use.

It is a further object of the invention to provide a closed aseptic system from process assembly to the end user.

It is yet a further object of the invention to provide a tissue culture chamber that will produce a uniform piece of three-dimensional tissue.

These objects are met by the provision of a growth chamber which comprises a casing with a substrate for growth of tissue disposed within the casing. In one embodiment, the casing has front, back, bottom, top and side walls defining a growth chamber. The chamber has an aseptic seal which maintains the chamber as a closed environment. The front and back have substrate anchoring mechanisms, such as a plurality of stand-off pins which maintain the proper spacing between the front and back walls and anchor pins and mating cavities which prevent the substrate from moving within the casing. The casing is preferably placed in a vertical position with an inlet port for the inflow of media proximate to the bottom of the casing and an outlet port for the outflow of media proximate to the top of the casing. The vertical position allows bubbles formed during tissue processing to be vented out the top of the chamber and thus eliminates the formation of bubbles in the chamber which could occlude growth of the tissue in the vicinity of the bubble.

Liquid media will flow from the bottom of the casing to the top, with even distribution facilitated by the provision of fluid distribution means disposed within the casing. A first flow distributor is located proximate to the inlet port, and a second flow distributor is located proximate to the outlet port. In the preferred embodiment, the flow distributors are baffles which have a greater height at the center, thus forcing the liquid to flow to the side walls of the casing where the baffles have a decreased height. Each baffle includes an extending block portion directly proximate to the inlet or outlet port to help distribute the flow upon entry and exit.

In an alternative embodiment, the chamber primarily comprises a cassette formed from a base portion and a cover portion which may be joined by at least one hinge or other closure means so that the cover portion may be separated from the base portion. Tissue scaffolds are preferably placed directly on the surfaces of the base portion and the cover portion for culturing so as to minimize the amount of exposed cassette surface upon which cells may attach during culturing.

The cassette includes at least two ports which are used for the introduction and removal of fluids that are provided to the tissue. The cassette also includes an o-ring gasket which provides a reliable hermetic seal between the base portion and cover portion. The o-ring may be retained in an undercut channel located in the four corners of either the cover portion or the base portion.

The cassette may also include a latch which facilitates the safe opening and closing of the cassette during final application of the tissue, or a thumbstrap which facilitates the handling of larger sized cassettes. A retaining band may also be used for the reliable closure and easy opening of the cassette. The retaining band may be undersized in relation to the cassette so as to create external closing pressure on the cassette halves when placed on the cassette.

In accordance with the invention, tabs may also be placed on the inner surface of both the base portion and the cover portion of the cassette. The tabs may be attached to the cassette with sufficient strength to prevent inadvertent detachment of the tab from the cassette, but not with so much force that would prevent removal by comfortable hand force.

When the scaffold is to be removed from the cassette for use, the user need simply press down on the tabs, which will in turn cause the outer edge of the tab to lift away from the cassette surface. The user then peels the tab away from the cassette, lifting the attached scaffolding from the cassette surface.

During culturing, the cassette is preferably placed in a vertical position with an inlet port for the inflow of media proximate to the bottom of the cassette and an outlet port for the outflow of media proximate to the top of the casing.

The vertical position allows bubbles formed during tissue processing to be vented out the top of the chamber and thus eliminates the formation of bubbles in the chamber which could occlude growth of the tissue in the vicinity of the bubble.

Liquid media will flow from the bottom of the cassette to the top, with even distribution facilitated through a combination of deflector plates, fluid distribution channels, and a flow channel. In accordance with the present invention, once fluid is pumped into the cassette through the inlet port, it enters the inlet fluid distribution channel. The purpose of the distribution channel is to ensure even distribution of the fluid from a point delivery source across the entire surface of the tissue scaffold. Deflector plates also ensure an adequately uniform flow profile by spreading out fluid from the inlet port across the complete width of the flow channel. Once the fluid has crossed the flow channel and the scaffold, it enters the outlet distribution channel and exits the outlet port. In this manner, a uniform environment for the culturing of tissue scaffolding is provided.

In an alternative embodiment of the present invention, multiple flow channels may be included in one cassette. In this embodiment, any number of individual chambers may be included together in a cassette such that multiple scaffolds may be cultured at one time.

In yet another alternative embodiment of the invention, the cassette is cylindrically shaped and the substrate disposed within the cassette is spiral shaped. In this embodiment, distribution plates may be used to distribute media flow evenly and to maintain the spiral shape of the substrate.

BRIEF DESCRIPTION OF THE DRAWINGS

These and other features, aspects, and advantages of the present invention will become more readily apparent from the following detailed description, which should be read in conjunction with the accompanying drawings in which:

FIG. 3A is a perspective view of a baffle;

FIG. 4 is a perspective view of the chamber;

FIGS. 7A–7B illustrate an alternative exemplary embodiment of a casing for growing three dimensional tissue cultures, wherein FIG. 7A is a perspective view of a casing laid open and FIG. 7B is a perspective view of a closed casing;

FIGS. 9A–9D illustrate a closure system for a casing, wherein FIG. 9A is a top perspective view of a retaining band, FIG. 9B is a bottom perspective view of a retaining band, FIG. 9C is a top plan view of a retaining band, and FIG. 9D is a perspective view of a retaining band on a casing;

FIGS. 10A–10B illustrate a device for ensuring easy access to a tissue scaffold, wherein FIG. 10A is a top plan view of a casing with tabs, and FIG. 10B is a partial cross-sectional view of a casing with tabs;

FIGS. 11A–11B illustrate a fluid distribution system within a casing, wherein FIG. 11A is a side view of the system and FIG. 11B is a cross-sectional view of the system;

FIGS. 14A–14F illustrate various embodiments of endplates for a cylindrical cassette, wherein FIG. 14A is a plan view of an endplate with a spiral groove, FIGS. 14B–14D are alternative exemplary embodiments of endplates with perforations for evenly distributing fluid flow, FIG. 14E is a cross-sectional view of conically-shaped endplate, and FIG. 14F is a cross-sectional view of a plate-shaped endplate.

DETAILED DESCRIPTION OF THE INVENTION

Figure 1:
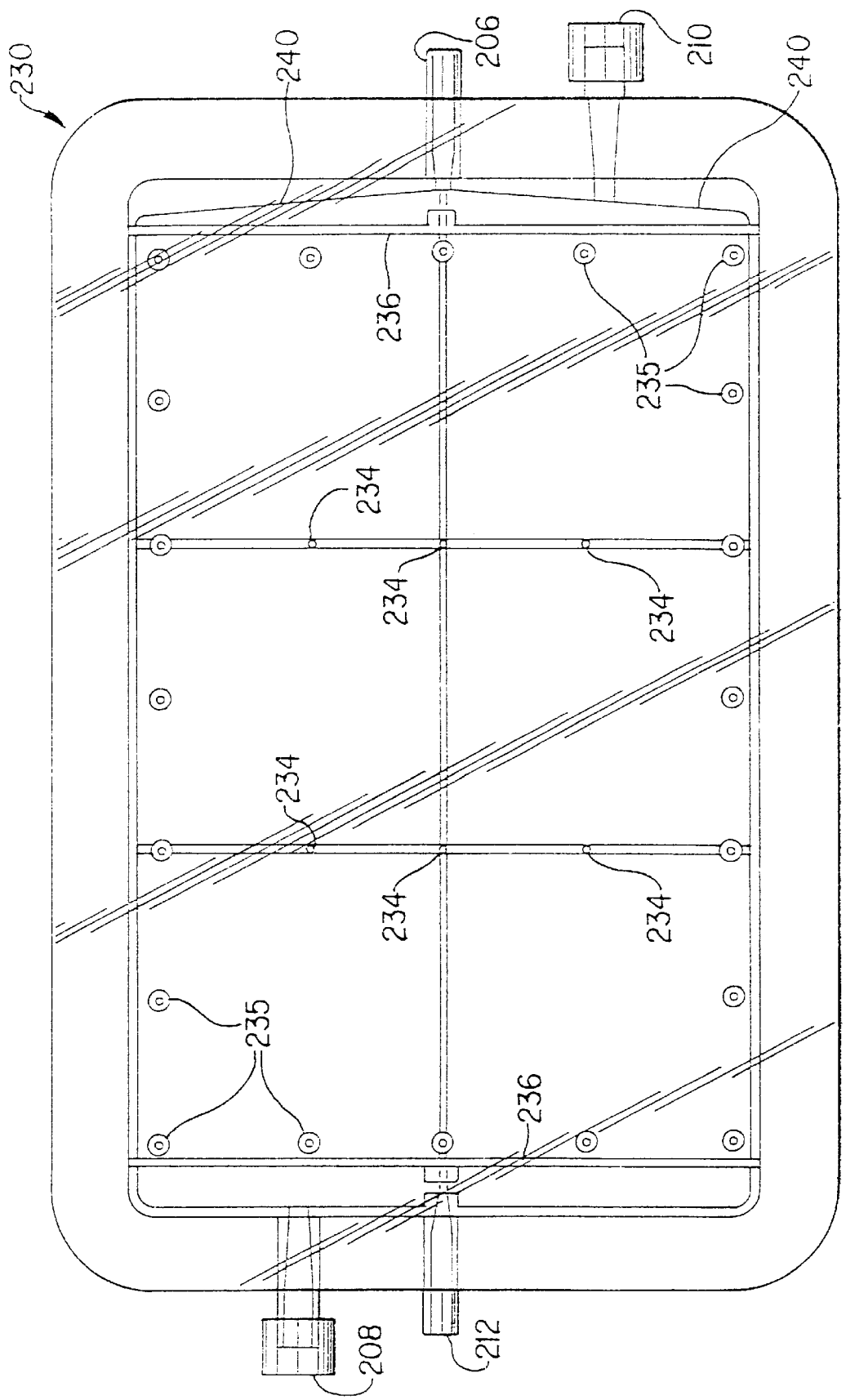
FIG. 1 is a top plan view of the base portion of the casing.

The following embodiments of the present invention will be described in the context of an apparatus for aseptically culturing three-dimensional tissue, although those skilled in the art will recognize that the disclosed methods and structures are readily adaptable for broader application. Note that whenever the same reference numeral is repeated with respect to different figures, it refers to the corresponding structure in each such figure.

Figure 2:
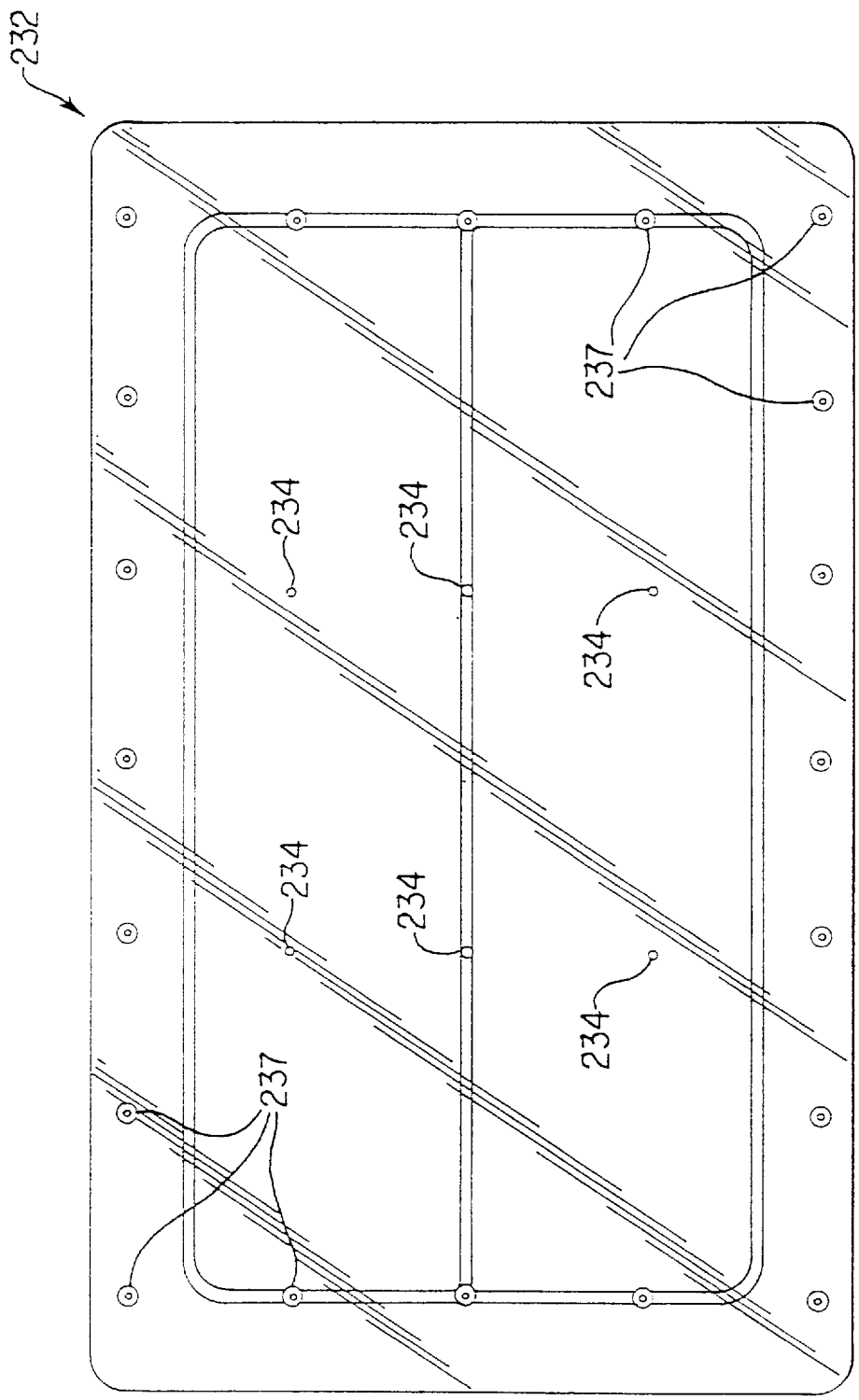
FIG. 2 is a top plan view of the front wall of the casing.

The growth chamber of a first embodiment of the present invention includes a casing formed from the base portion 230 shown in FIG. 1, and the cover portion which is the front wall 232, shown in FIG. 2. The base portion 230 includes the back wall, two side walls, and the top and bottom walls. The base portion 230 and front wall 232 are preferably manufactured from a rigid material that can maintain a sterile environment, inhibit cell growth directly on the material, and provide a fluid environment conducive to cell growth, such as a rigid or semi-rigid plastic. The base portion 230 and the front wall 232 are joined by at least one hinge or other closure means of any type desired, so that front wall 232 can be raised as shown in FIG. 4, or otherwise separated from the base. FIG. 4 illustrates that the base portion 230 and front wall 232, when joined, create a casing 200 in which substrate 202, which will be further described below, is placed to create the chamber 204 for the growth of tissue.

The base portion 230 and front wall 232 can be manufactured in a wide variety of sizes, depending on the desired size of the tissue to be grown. For example, in this embodiment, a 4 by 6 inch size is preferable for use in growing skin tissue for treating burn wounds as it is a convenient size for physicians in that application. The preferable size for chronic ulcer wounds is significantly smaller, 2 by 3 inches for example. Other sizes will be determined as appropriate for a specific product and application as required by the market. Many other sizes and configurations are possible with the identical production system by changing the cassette dimensions and arrangement.

The casing 200 has at least two processing connections and two user connections (206, 208, 210, 212) for aqueous fluid transport which can be located on the base portion 230 as shown in FIG. 1. The processing and user connections could be designed to be the same connections, so that the casing 200 would have only one connection proximate to the bottom and only one connection proximate to the top of the casing. The center ports 206, 212 are used for the introduction and removal of media and any other fluids that are provided to the tissue. In the preferred embodiment, the casing 200 is placed in a vertical position during the production of tissue. Therefore, the input port 212 is provided at the center of the bottom of the casing 200, and output port 206 is at the top of the casing. Side ports 208, 210, are sealed during the production of tissue, and are provided for subsequent use by medical personnel for rinsing tissue prior to application of the tissue on a patient.

A mechanism for substrate anchoring and centered placement is required. In the preferred embodiment, the back wall of the base portion 230 and front wall 232 are provided with stand-off pins 234 near the center of the casing 200 to maintain the proper spacing between the substrate 202 and the back of base portion 230 and front wall 232. Anchor pins 235 in the base portion 230 and mating cavities 237 in the front wall 232 are also provided to prevent the substrate 202 from shifting. However, one skilled in the art will understand that other mechanical means for anchoring are acceptable.

Approximate plug flow of medium entering near the bottom and leaving near the top of the chamber 204 is necessary for the growth of continuous and uniform tissue. In the preferred embodiment, two baffles 236 are located on the back of base portion 230 of the casing 200 to force the flow to spread to the edges of the casing. Each baffle 236 is located proximate to each end of the casing 200. Each baffle 236 (shown enlarged and exaggerated in FIG. 3A) is part of the design to provide an approximate plug flow of medium entering the bottom and leaving the top of the chamber.

In the preferred embodiment, each baffle 236 has a greater height (indicated by arrows in FIG. 3A) in the center than at each end. The shape of the baffle 236 provides a very narrow gap between the baffle 236 and the bottom center of the casing and between the baffle and the top center of the casing. These front and back gaps become larger towards both sides of the casing due to the thinning of the baffle. The net effect is to move liquid which enters in the center of the casing through inlet port 212 towards the side walls in such a way as to cause a uniform upward flow without dead spots in the corners. Uniform distribution of the liquid is necessary for the growth of a continuous and uniform portion of tissue. The height of the baffle 236 preferably only varies by approximately 0.05" from the center to either end. In the preferred embodiment, for a casing size of 4 by 6 inches, the baffles are 4 inches in length to meet with the side walls of the inside of the casing, and have a height of 0.115" at the center portion, and a height of 0.062" at either end. The baffles also preferably have a thickness of approximately 0.062". The inside of the casing is approximately 0.125" between the base and front wall, to allow 0.05" of space on each side of the baffle at the center.

An extending block portion 238 is provided on baffle 236, facing the inlet of the casing to further distribute flow. The same baffle arrangement is repeated at the top (outlet) of the casing with the addition of a shallow bevel 240 along the top corners towards the center outlet port to help direct liquid flow and any bubbles out of the casing.

Figure 3B:
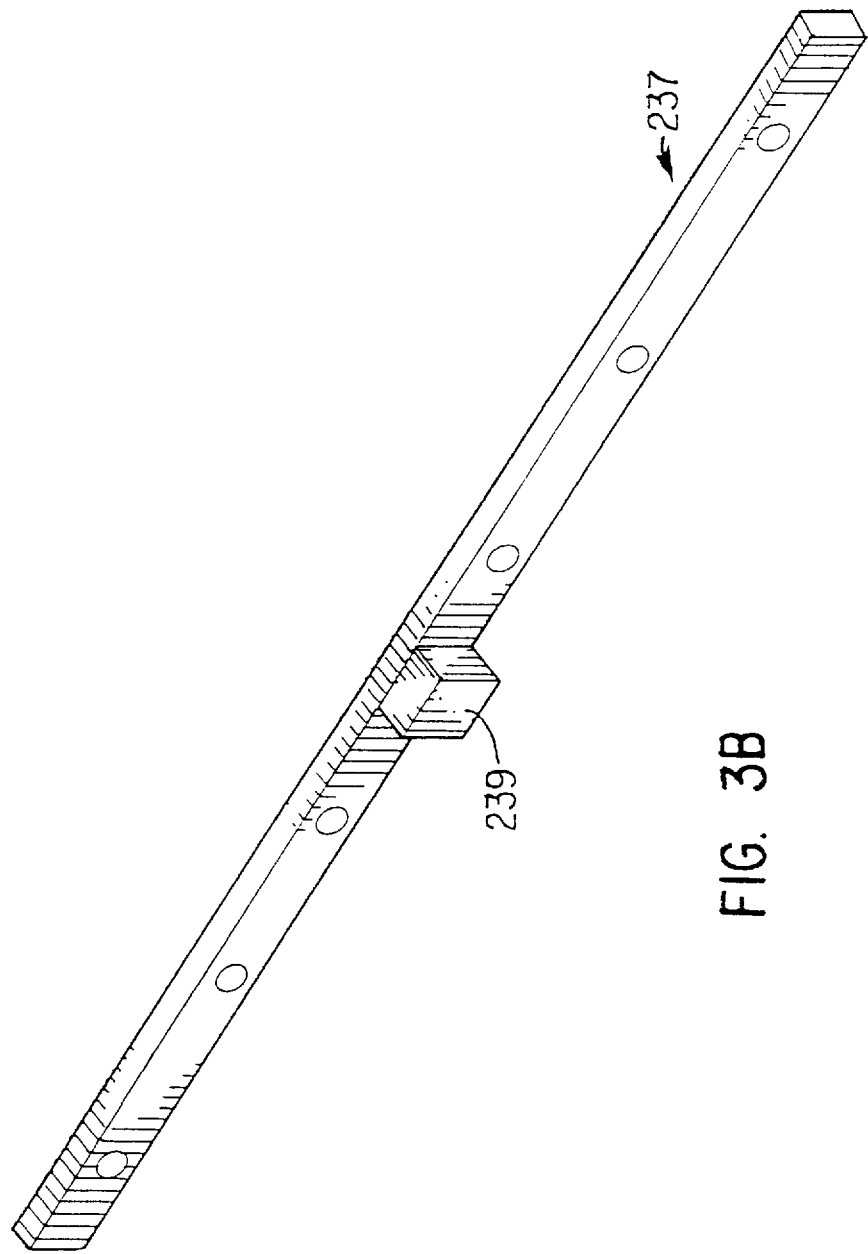
FIG. 3B is a perspective view of an alternative baffle.

Other potential shapes and configurations of the flow distributor could perform the same function, e.g., a perforated baffle with small holes in the center and larger holes near the sides. An alternative baffle design is shown in FIG. 3B, in which baffle 237 has an extending block portion 239 and a plurality of openings to distribute flow. The specific design shown in FIG. 3A was chosen due to ease of manufacture and handling. The baffle may be glued in place, welded, press fit, or may be formed as part of the base 230 or front 232. The only requirement is that it be held firmly in place during cell growth.

An assembled growth chamber 204 is shown in FIG. 4. Each chamber 204 has a substrate 202 which is preferably a mesh made of a biocompatible material, provided within the casing 200. Possible mesh materials include polyglactin (PGA) 910 mesh, which is produced by Ethicon, Inc., Somerville, N.J. In addition to the bioabsorbable PGA mesh, the system can also be used with a nylon and silicon rubber combination (Biobrane™, which is produced by Dow-Hickam). The silicone rubber membrane serves as an artificial epidermis in use, and only requires a growth system in which media only flows on one side of the material, much more flexible than the PGA and is supported on an additional polycarbonate sheet with holes pre-cut to fit over the anchor pins 235 in the casing 200. Alternatively, when using Biobrane™ material in the casing, the anchoring pins can be omitted and the Biobrane™ material can be placed directly on the inside of the back 230 or the front 232, or both. Placing a piece of Biobrane™ material on each side will increase efficiency in tissue production as it only requires media flow on one side, thus enabling simultaneous processing of two pieces in the chamber. One additional version of the system may be used with a "felted" non-woven material and human chondrocytes to produce cartilage products. Other tissue types and support structures are possible within the scope of this invention.

As shown in FIG. 4, chamber 204 includes the casing 200, which is formed by joining the base portion 230 with the front wall 232 by a hinge arrangement. The hinged front can be opened using lifting tab 214. The closing seal of the chamber 204 must be a sterile, water-tight seal, but must also allow easy opening by the nurse or doctor for use. A preferred sealing arrangement consists of layers of polyester film and a top seal that protects the aseptic nature of the chamber 204. This may be opened by cutting the seal with a knife or other sharp implement, allowing for convenient access by the end user. The chamber 204 is designed to permit sterilization by several methods including EtO, Gamma or E-Beam irradiation, or autoclave (the PGA mesh is not stable to this method). A preferred method is E-Beam irradiation.

Figure 5:
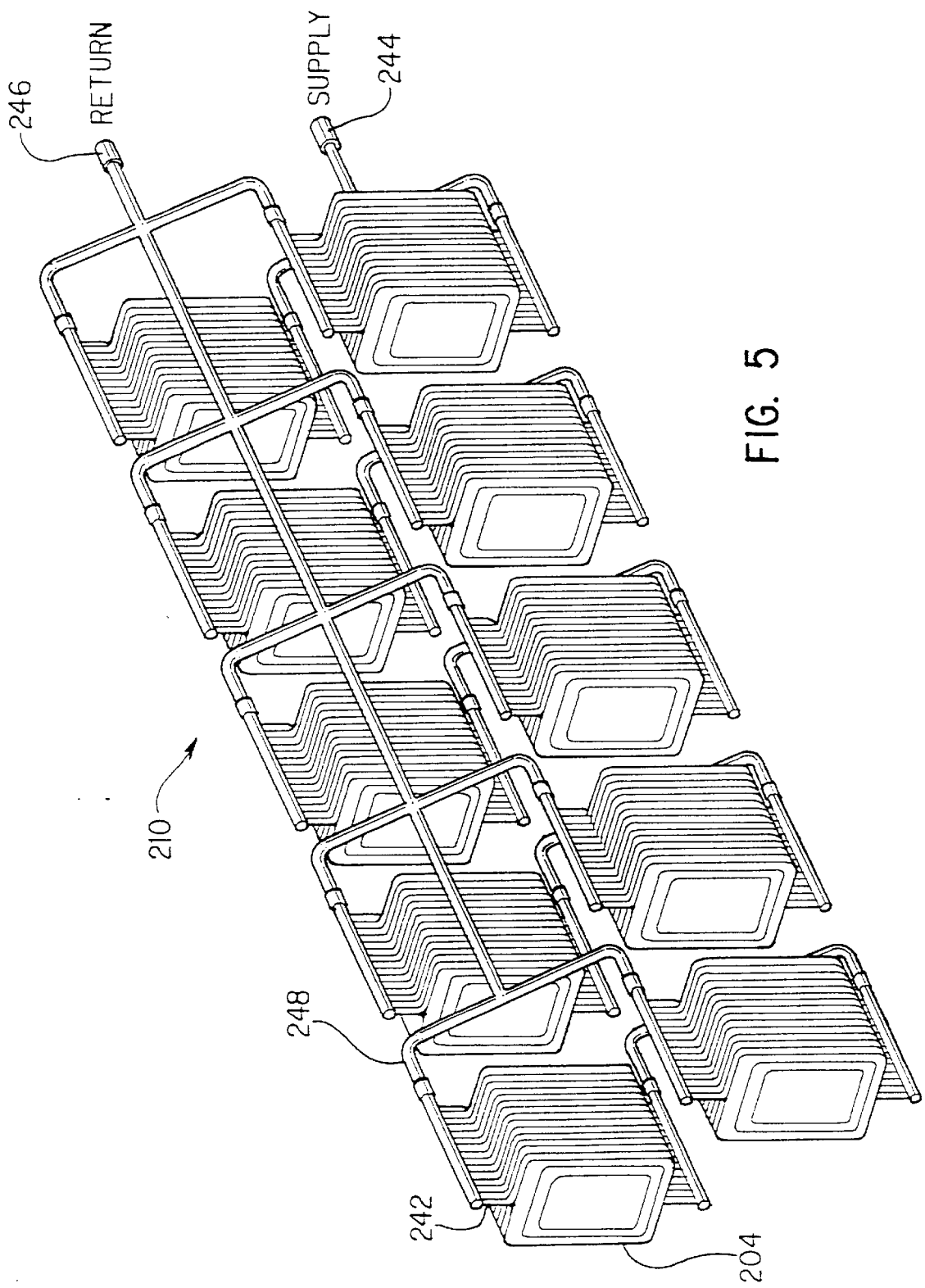
FIG. 5 is a diagram of manifolded chambers.

As shown in FIG. 5, the chambers 204 may be manifolded together. In the preferred embodiment, fifteen or more individual chambers may be manifolded together to form a stack. FIG. 5 illustrates ten of the stacks manifolded together to form manifold system 210. System 210 includes a fluid supply line 244 and a fluid return line 246. In order to ensure proper cell feeding and distribution of feeding liquids, a reliable fluid distribution system is required. In the preferred embodiment, the chambers 204 are manifolded together such that there is a pressure drop between each chamber and the large manifold line 248. In order to create the drop in pressure, a small length of precision bore, narrow diameter tubing 242 is used. Uniform distribution of liquid flow to each chamber is accomplished by the pressure drop across a narrow length of restriction tubing leading to the entrance port of each chamber. The restriction tubing 242 is a few inches long (1–6) and has an inside diameter in the range of 0.015 inch to 0.095 inch. In general, the optimum diameter and tolerances of the restriction tubing depends upon the actual flow rate and diameter of the manifold line. A preferred embodiment of the restriction tubing has approximately the following dimensions: ID=0.031 in, OD=0.188 in, length=2 in. At a 5 ml/min flow, these dimensions result in a pressure drop of approximately 2.25 inches of water or 0.08 PSI. A minimum pressure drop of 2.0 inches of water is desirable to alleviate the effect of high velocity fluid at the entrance of the growth chamber. A conventional liquid process might use a narrow orifice such as a pin hole or needle valve to establish such a pressure drop; however, such a device would not permit free flow of cells to pass through to the chambers during the seeding operation and might easily become clogged by cells or cell debris during the multiple week growth period of the tissue.

The method steps for production of three-dimensional tissue are described in U.S. Pat. No. 5,266,480 to Naughton et al., also assigned to the present assignee, and incorporated herein by reference.

Figure 6:
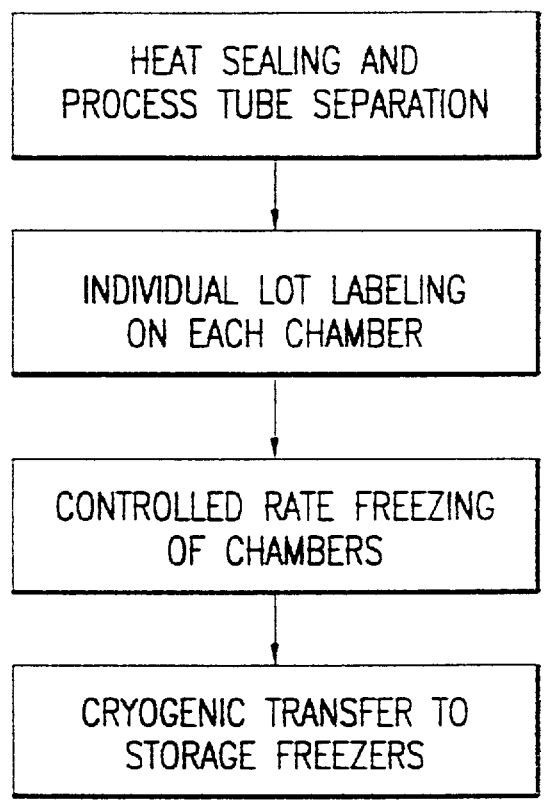
FIG. 6 is a flow chart of the steps for freezing and storage of the tissue within the chamber.

The Finishing/Freezing step of tissue production is illustrated in the flow diagram of FIG. 6. After the tissue is grown in the chamber 204, freezing solution is added, and the center ports 206, 212 used for feeding and draining of fluid medium are sealed off such as by heat sealing in order to maintain the aseptic nature of the chamber. The unique features of the chamber allow the tissue to be frozen and stored in the same container that it was grown.

After completion of tissue growth, the growth medium is removed and the product is rinsed with any solution adjusted to physiological pH and osmolarity such as phosphate buffered saline solution (PBS). After completion of the rinse step, the chambers 204 are filled with freezing solution consisting of a physiological pH buffering system, such as PBS and HEPES, which optionally may be also supplemented with one or more cryoprotectants such as DMSO, and ancillary agents such as FBS. Temperature is reduced during this process. The system connections are separated and individual chambers are removed by radio frequency welding (other methods could also be used, e.g. sonic welding or direct heat welding) at their upper and lower process tubing connections 206, 212. This method protects the integrity of the chambers 204 as the system remains completely closed and there is no potential for introduction of contaminants. The individual chambers can then be inspected, labeled, outer protective covering added, and frozen. More than a single freezing method may be used at this point. For relatively small numbers of chambers produced for clinical trials, simple freezing spread out in a freezer set at less than or equal to −70° C. is sufficient. For larger commercial scale applications large controlled rate freezing systems may be used. The specific freezing program will depend on the product format and size.

The product is stored in storage freezers at less than or equal to −70° C. until ready for use. The chambers 204 are sent to the users with the tissue sealed inside the chamber. When a chamber is desired to be used, it is first melted by placing in a warm temperature or warm water bath. The ports provided on the ends of the chamber (shown in FIG. 4 as 208 and 210) are attached to tubes. The freezing solution is drained, and saline is provided to the chamber and drained, to rinse the tissue, which can then be used by medical personnel.

Figure 7A:
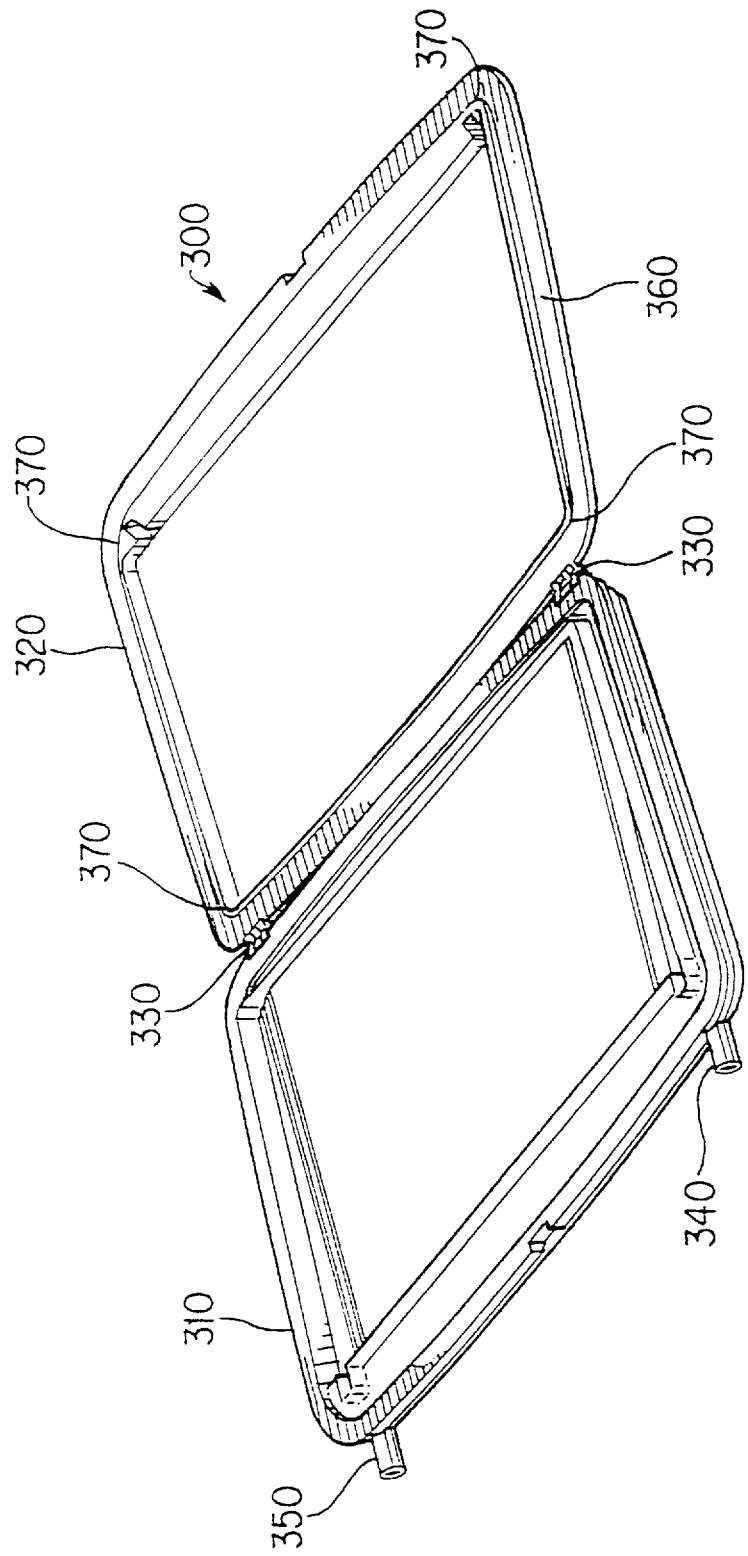
Figure 7B:
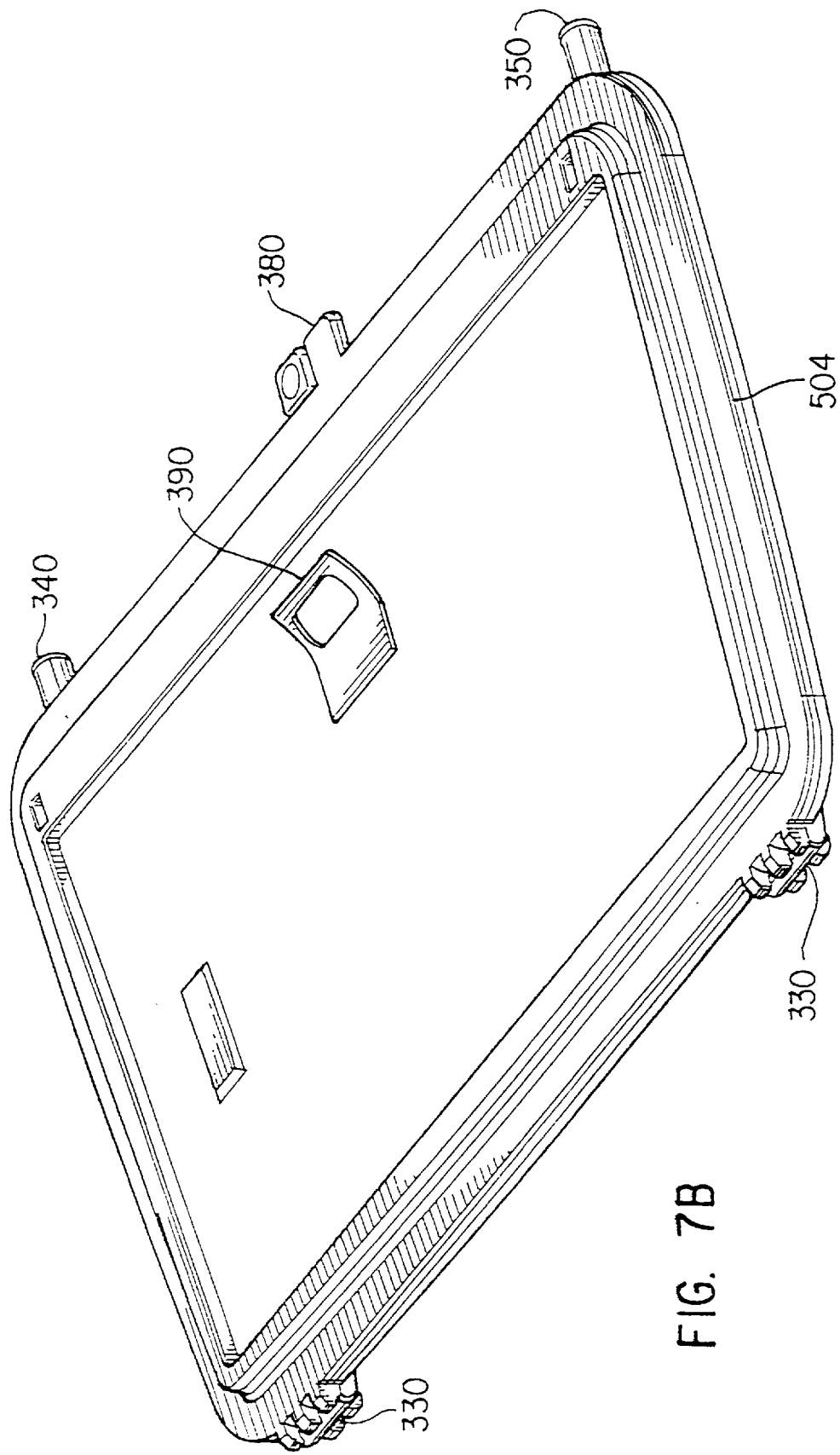

FIGS. 7A–7B disclose an alternative exemplary embodiment of a growth chamber for culturing three dimensional tissue. According to this alternative embodiment of the invention, the chamber primarily comprises a cassette 300 formed from a base portion 310 and a cover portion 320, both of which are shown in FIG. 7A. The base portion 310 includes a bottom wall, two side walls, and front and back walls. The cover portion 320 also includes a top wall, two side walls, and front and back walls.

The base portion 310 and the cover portion 320 may be joined by at least one hinge 330 or other closure means of any type desired, so that the cover portion 320 may be separated from the base portion 310. As shown in FIG. 7B, the base portion 310 and cover portion 320, when joined in conjunction with o-ring, create a closed chamber in which a tissue scaffold 400 may be placed for the growth of tissue.

Cassette 300 includes at least two ports 340 and 350 for fluid transport which may be located on the base portion 310 (as shown in FIG. 7A) or the cover portion 320. Ports 340 and 350 are used for the introduction and removal of media and any other fluids that are provided to the tissue.

The apparatus also includes an o-ring 360 which provides a reliable hermetic seal between base portion 310 and cover portion 320. A method is provided in the preferred embodiment to hold o-ring 360 in place on either the cover portion 320 (as shown in FIG. 7A) or alternatively the base portion 310. Specifically, o-ring 360 may be retained in an undercut channel 370 located in the four corners of either the cover portion, as shown in FIG. 7A, or the base portion 310. This structure is advantageous as inadvertent contact between a loosely fitting o-ring and the delicate tissue contained in the growth chamber is undesirable.

FIG. 7B discloses additional features that facilitate the safe opening and closing of cassette 300 during final application of the tissue. Latch 380 enables the user to apply only a small amount of force to open the cassette. The design of latch 380 can be varied, but preferably should be sized to enable easy manipulation by the adult hand. As shown in FIG. 7B, latch 380 may be comprised of two members, one extending from the cover portion 320 and one extending from the base portion 310. In addition, a thumbstrap 390 may be used to facilitate handling of larger sized cassettes. Thumbstrap 390 may be a curved member extending outwardly from either the cover portion (as shown in FIG. 7B) or the base portion.

The base portion 310 and cover portion 320 are preferably manufactured from a rigid, biocompatible material which is able to maintain structural and compositional integrity under the sterilization/cultivation and freeze/thaw cycles which were previously described, and which are further described below in relation to this alternative exemplary embodiment. In short, cassette 300 must be able to withstand irradiation, chemical, or thermal treatments to sterilize the growth chamber prior to culturing. In addition, the cassette 300 should preferably withstand freezing and storage at temperatures less than −20° C., which is required to preserve the cultured tissue, as well as subsequent thawing to room or body temperature once the tissue is required for use. If a stagnant fluid system is to be employed during culturing, cassette 300 should also be gas permeable.

Any materials which meet the above-specified requirements may preferably be considered for construction of cassette 300. Examples of acceptable materials include polycarbonate, Teflon, PVC, high density polyolefins, and stainless steel, with polycarbonate being most preferable due to its low cost, ease of molding and optical clarity.

O-ring 360 is preferably manufactured from any elastic, biocompatible material, such as viton, Teflon, Gortex, silicone rubber, polyurethane or natural rubber, that has mechanical properties sufficient to ensure a robust seal.

Base portion 310 and cover portion 320 may also be manufactured in a wide variety of sizes, depending on the desired size of the tissue to be grown. For example, a 5 by 7.5 inch size is preferable for use in growing skin tissue for treating burn wounds as it is a convenient size for physicians in that application. However, the preferable size for chronic ulcer wounds is significantly smaller, 2 by 3 inches for example. Other sizes may be determined to be appropriate for a specific product and application as required by the market, and would still fall within the scope of this invention.

Figure 8:
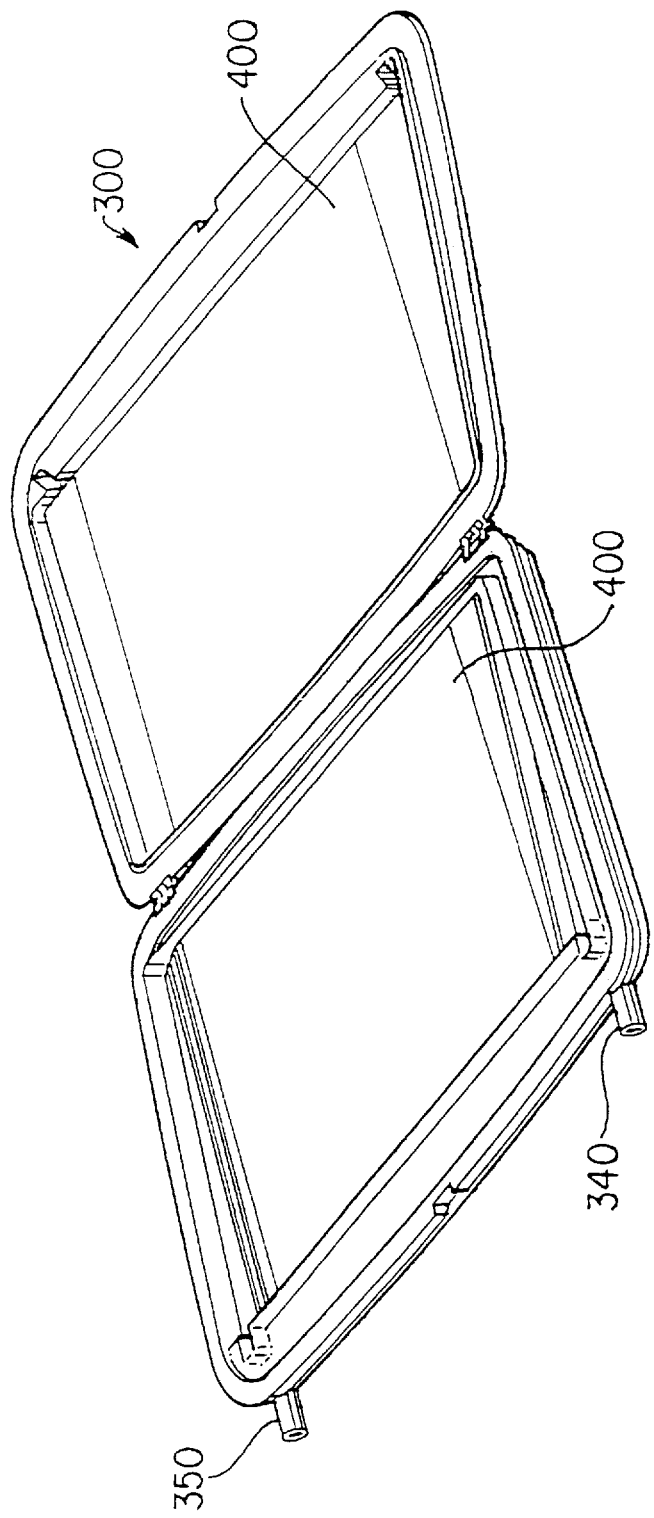
FIG. 8 is a perspective view of a casing including tissue scaffolds.

As shown in FIG. 8, certain tissue scaffolds 400 (e.g., Biobrane™ available from Dow-Hickam) may be placed directly on the surfaces of base portion 310 and cover portion 320 for culturing of tissue in this alternative embodiment. No mechanism for substrate anchoring and placement is required for these scaffolds. This is advantageous as cassette 300 may be produced in a compact form so as to maximize space efficiency for commercial growth, freezing, and final storage.

Scaffolds 400 may be retained to the inside surface of cassette 300 with or without application of external force via a retaining mechanism. However, in the preferred embodiment, the scaffolds 400 are spread across the cassette surface without an external retaining feature. Adequate adhesion is maintained by inherent physical attractive forces, primarily electrostatic and hydrophobic forces, between the scaffold and cassette surface.

A significant benefit of this design is the substantial improvement in the efficiency of the costly cell seeding process. Tissue utilized in transplant applications, such as non-transformed animal cell lines, requires attachment to a surface for viability and growth. These cells will attach to most biocompatible surfaces, including the cassette surface. Thus, it is desirable from cost and efficiency standpoints to minimize the area of internal cassette surfaces which are not covered by the tissue scaffold material. Minimization of exposed cassette surface is also desirable from a fluid dynamics perspective. This is so because, in the embodiment disclosed in FIGS. 7–11, more even fluid flow and distribution may be attained over a textured surface, such as Biobrane, than that which may be attained over a smooth surface such as the internal cassette surface. Accordingly, in a preferred embodiment, in which the scaffold is directly placed on the inner surface of cassette 100, the ratio of "active" internal area (covered by scaffold material) to total projected internal area should be greater than 75%, although lower percentages are contemplated to fall within the scope of the invention.

Figure 9A:
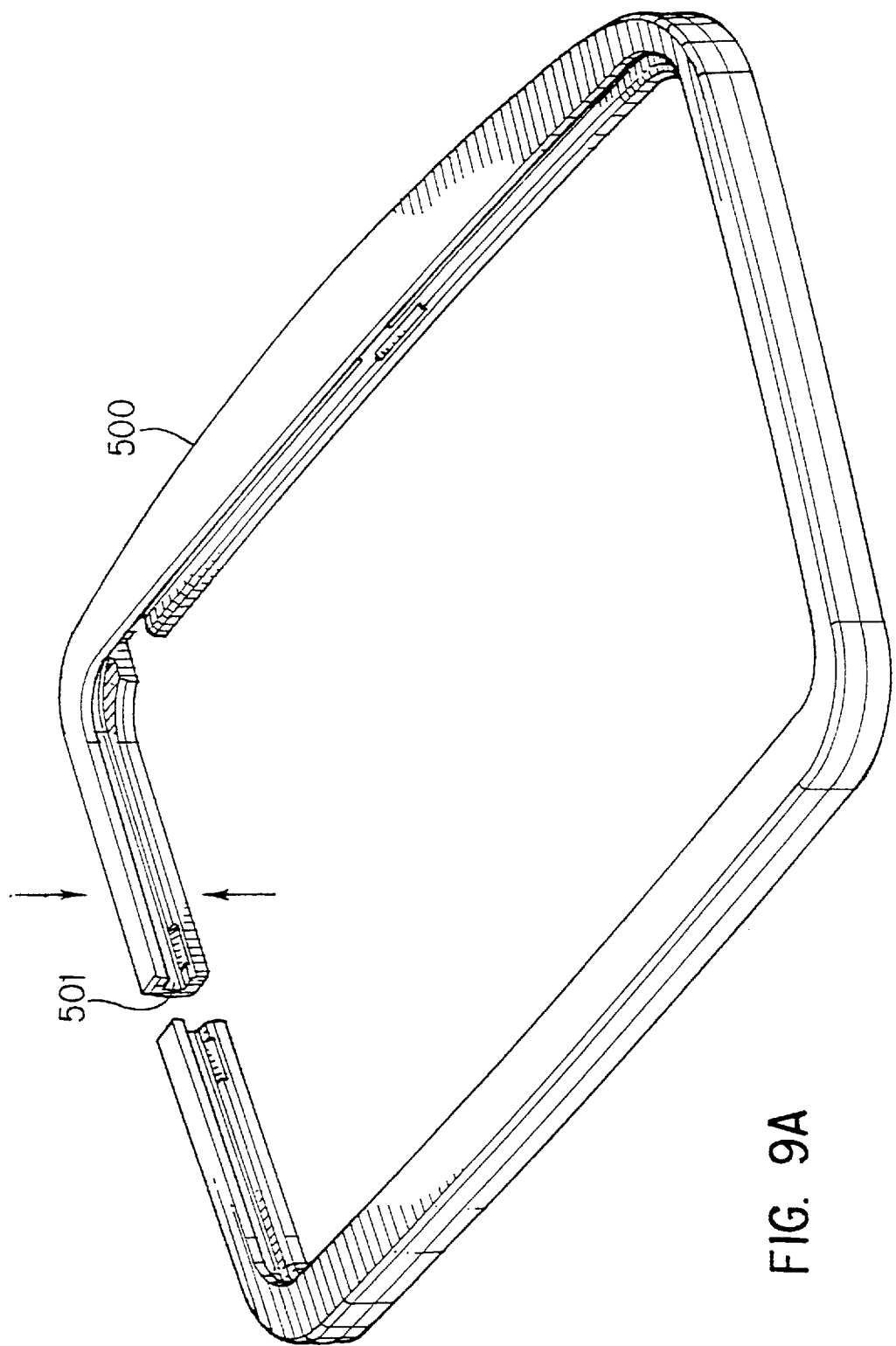
Figure 9B:
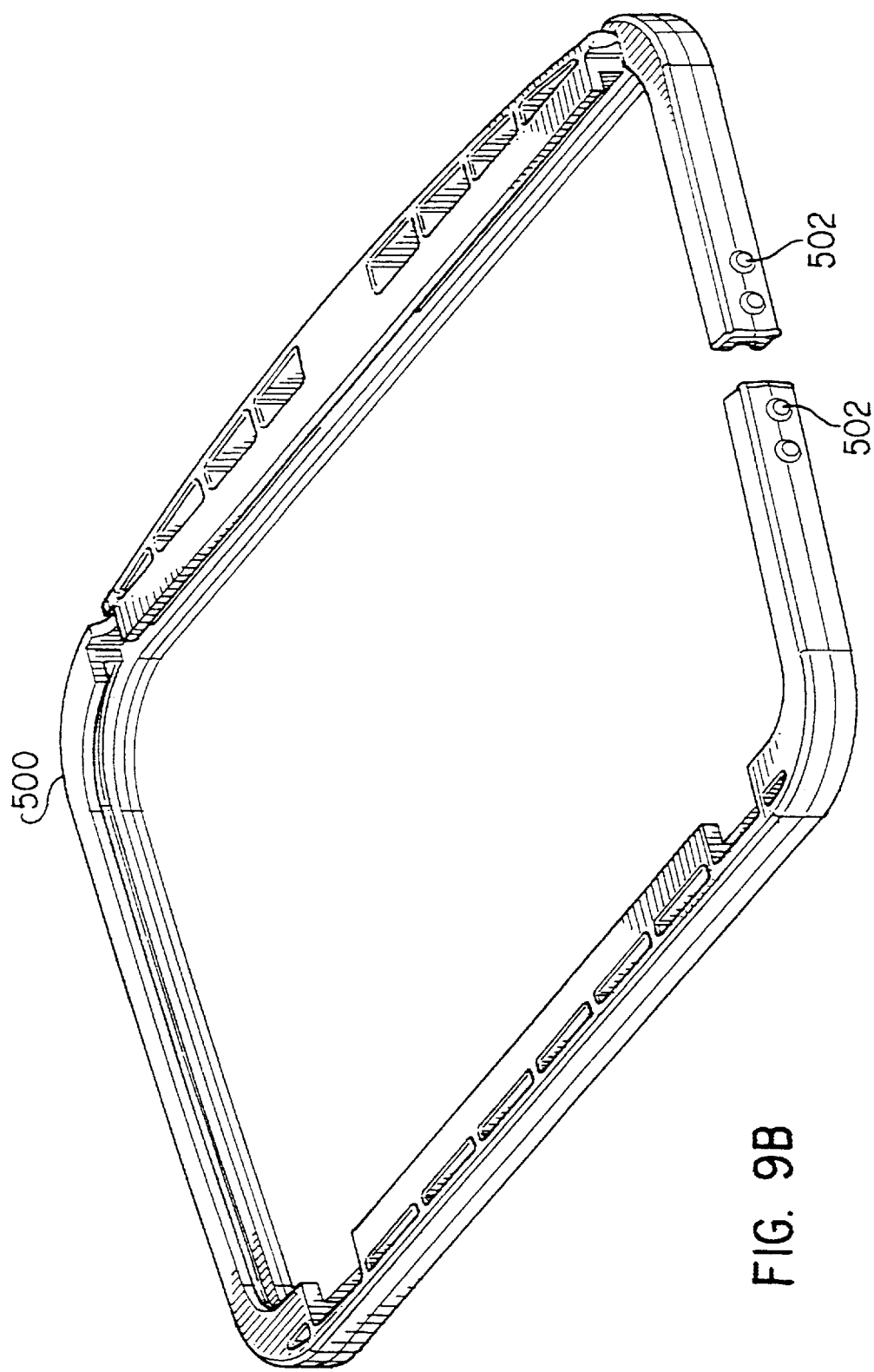
Figure 9C:
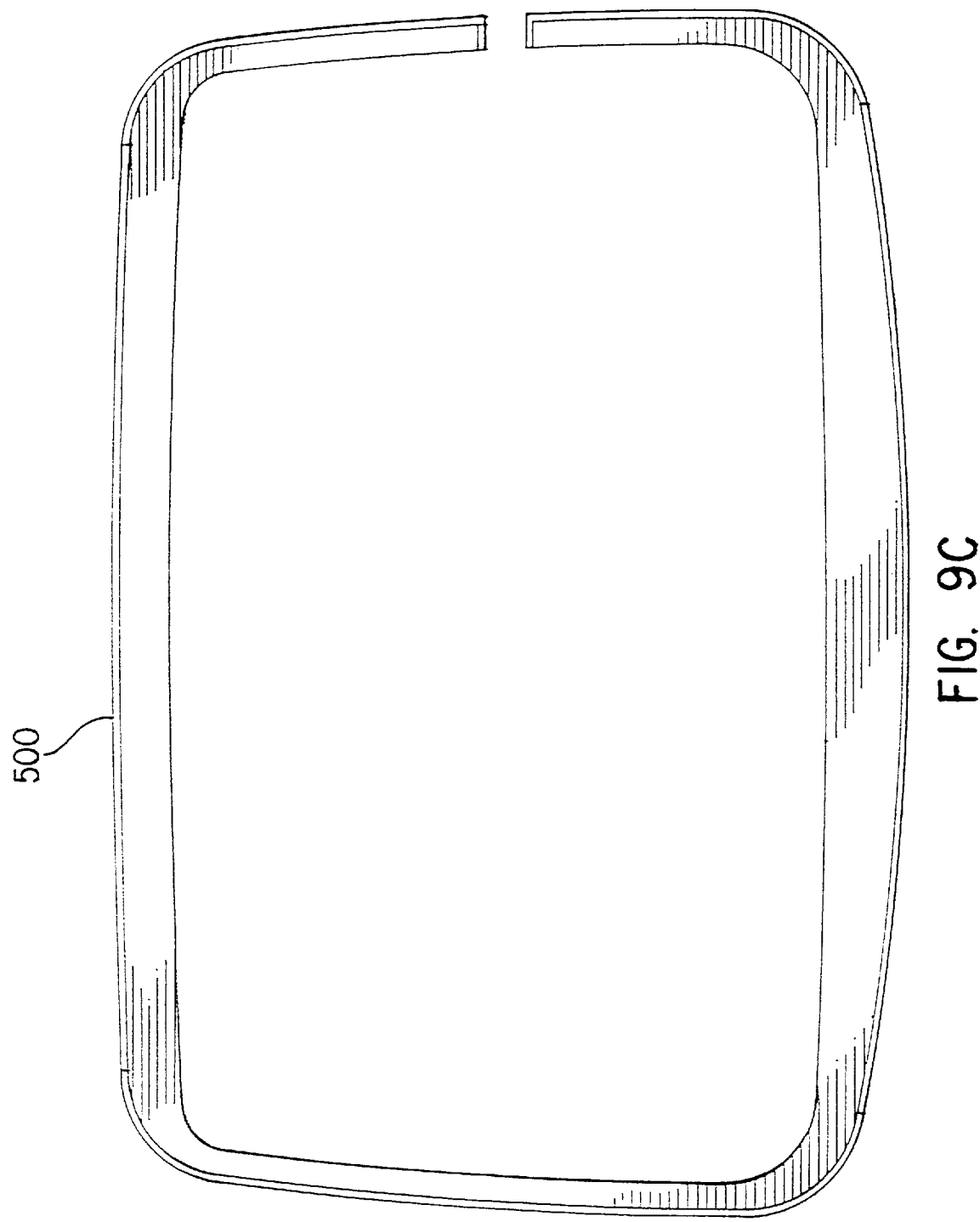
Figure 9D:
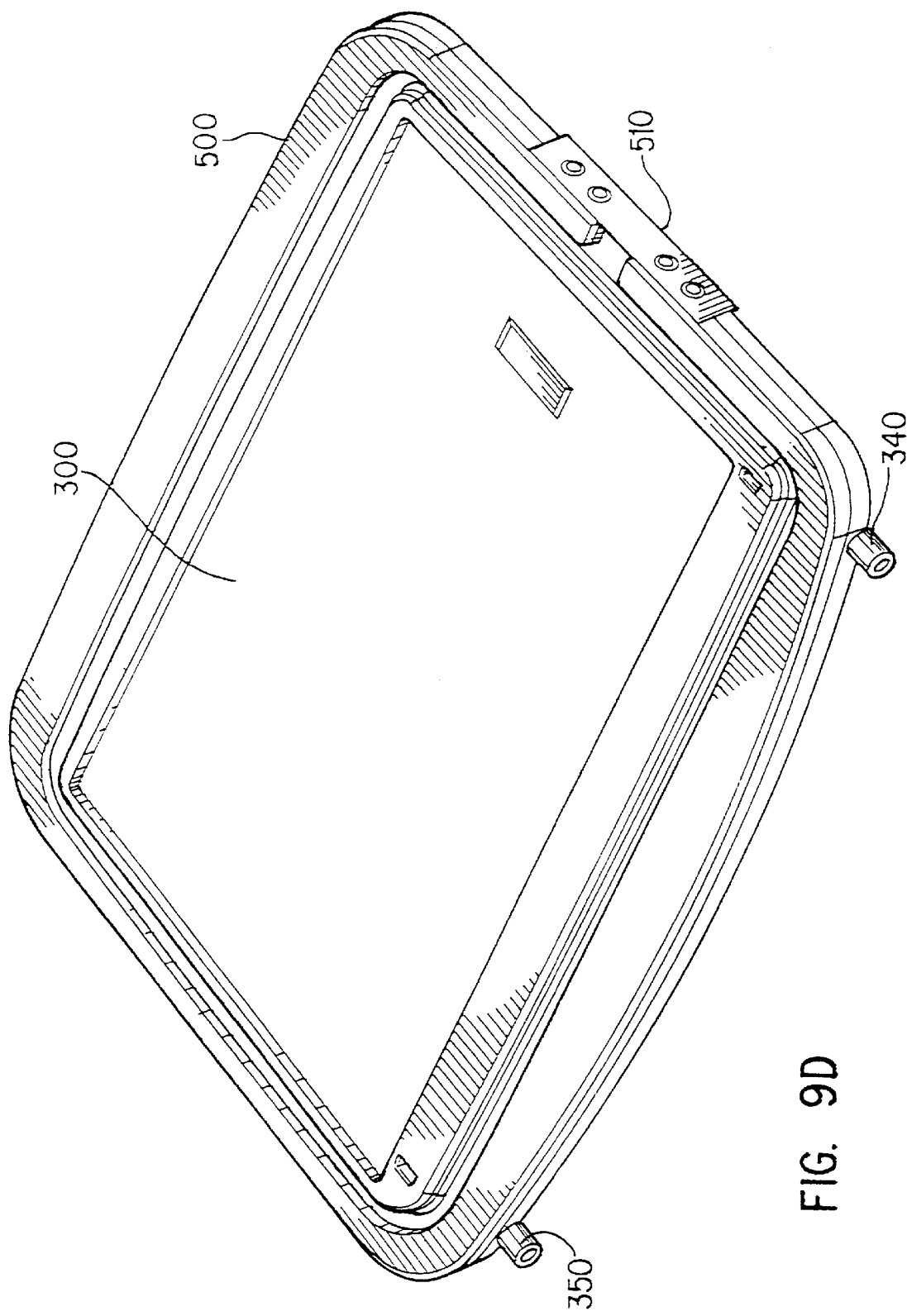

As shown in FIGS. 9A–9D, a retaining band 500 may be used for the reliable closure and easy opening of cassette 300. As shown in FIGS. 9A–9D, Retaining band 500 is a rectangular band with an inwardly directed annular groove 501. Retaining band 500 may be preferably comprised of an elastomeric material, and may be preferably undersized in relation to the combined width of the cassette and the uncompressed o-ring combination so as to create external closing pressure on the cassette halves 310 and 320 when placed on the cassette as shown in FIG. 9D (the direction of the closing pressure is shown by the arrows in FIG. 9A). Cassette halves 310 and 320 together define an annular ridge 504 (shown in FIG. 7B) over which retaining band 500 is placed.

The amount of undersizing of retaining band 500 is dependent upon the physical properties of the retaining band material and the desired maximum burst pressure for the cassette. However, in a preferred embodiment, the combination of an elastomeric polyester (Hytrel) retaining band 500 and approximately 0.03" undersizing, in relation to the combined width of the cassette and uncompress o-ring combination, results in maintenance of an adequate burst pressure in excess of 5 psi.

As shown in FIG. 9D, when retaining band 500 is in place, it maintains a uniform seal around the entire cassette, including such external features as hinges and tabs. As also shown in FIG. 9D, easy removal of retaining band 500 may be made possible through the use of a strap 510 which holds retaining band 500 in place around the cassette by attachment to studs 502 located on band 500. Strap 510 may be easily removed by being manually pulled away from studs 502, thus allowing for easy removal of band 500 from the cassette.

Figure 10A:
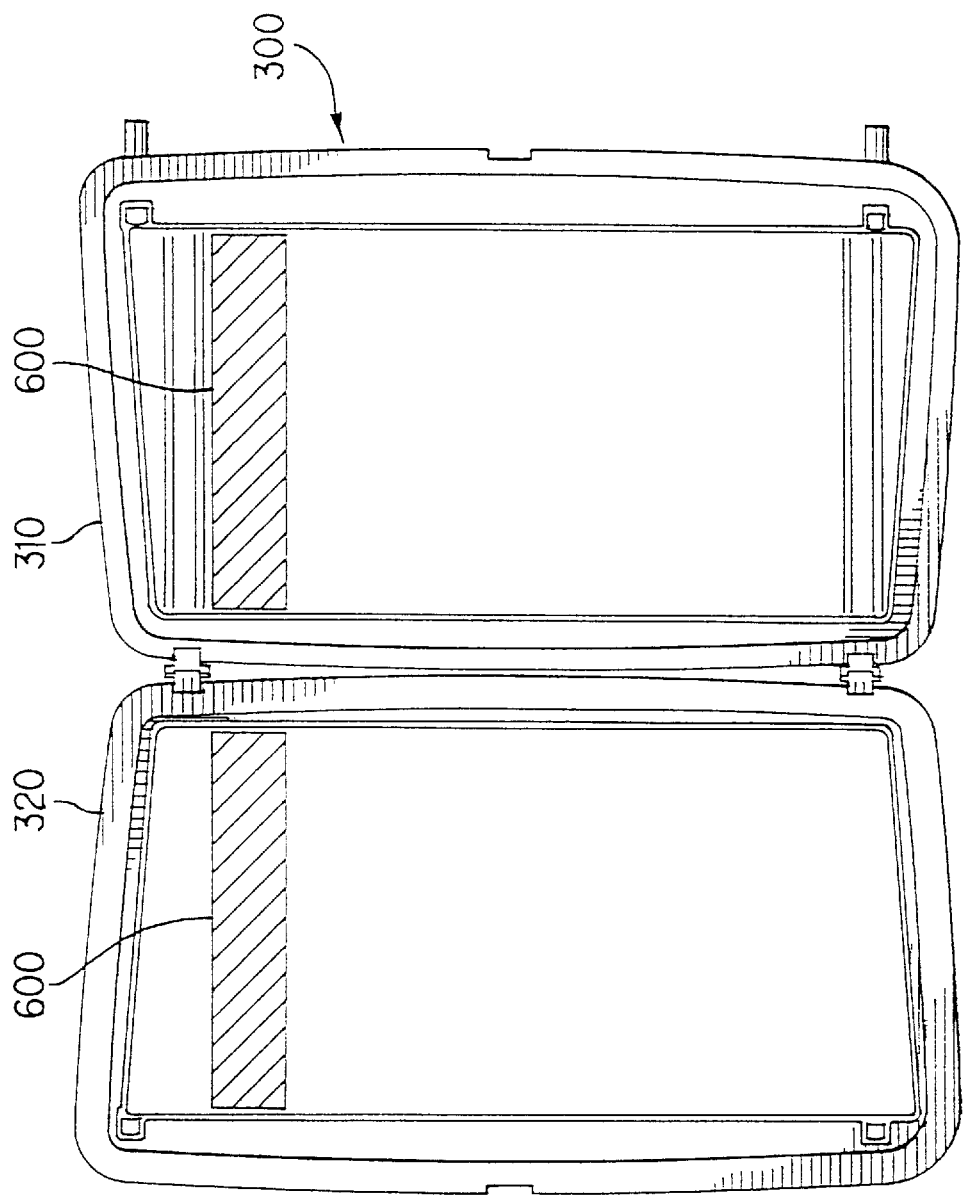

As noted, it is important that cassette 300 be constructed in a manner which enables easy access and sterile use of the tissue transplant. FIGS. 10A–10B illustrate one feature which facilitates such use. As shown in FIGS. 10A–10B, tabs 600 may be placed on both the base portion 310 and cover portion 320 of cassette 300, and may be comprised of any biocompatible, flexible material such as plastic. Although tabs 600 shown in FIG. 10A are placed on the outlet side of cassette 300, it is to be understood that tabs 600 may be placed anywhere on the cassette halves (including by the inlet side), and more than one tab per cassette half may be used.

As shown in FIG. 10B, tabs 600 are placed in a recessed area of the cassette so as to form a uniform internal cassette surface without ridges on which the scaffolding may be placed. The tab must be attached to the cassette with enough force to prevent inadvertent detachment of the tab from the cassette, but not with so much force that would prevent removal by comfortable hand force. Attachment by a biocompatible adhesive or other retaining mechanism, such as staking tabs using direct heat or ultrasonic energy, is desirable. When scaffold 400 is to be removed from cassette 300 for use, the user need simply press down on the tab 600 at groove 602 in the cassette, which will in turn cause the outer edge of the tab to lift away from the cassette surface (as shown by the dotted tab outline in FIG. 10B). The user then peels the tab away from cassette 300, lifting the attached scaffolding from the internal cassette surface in the process. Once the entire scaffolding has been lifted from the cassette surface, tab 600 may be separated from the scaffolding and discarded. In this manner, rapid and sterile removal of scaffold 400 from cassette 300 is facilitated.

As mentioned, cassette 300 may hold more than one tissue Scaffold 400. Tissue scaffolds 400 are preferably a nylon and silicon rubber combination (Biobrane™). The Biobrane™ material is much more flexible than the PGA and can be placed directly on the inside surface of cassette 300. Placing a piece of Biobrane™ on each cassette half will enable the simultaneous culture of 2 pieces of tissue of one bioreactor, thus increasing the efficiency of tissue production. however, it is to be understood that other tissue types and support structures are possible within the scope of this invention.

The growth chamber defined by cassette 300 is designed to permit sterilization by several methods including EtO, Gamma or E-Beam irradiation, or autoclave (the PGA mesh is not stable to this method).

Seeding and culturing of tissue scaffold 400 in the growth chamber defined by cassette 300 is generally accomplished by known techniques, with the added benefits and advantages gained from the relatively uniform fluid flow achievable with the systems according to the present invention. Examples of suitable seeding and culturing methods for the growth of three-dimensional cell cultures are disclosed in U.S. Pat. No. 5,266,480, which is incorporated herein by reference. The techniques described in U.S. Pat. No. 5,266, 480 for establishing a three-dimensional matrix, inoculating the matrix with the desired cells, and maintaining the culture may be readily adapted by a person of ordinary skill in the art for use with the present invention.

As mentioned, during culturing it is critical to maintain a constant environment across scaffold 400 to promote even development of the tissue. Biochemical, biological and physical properties of the final tissue culture which may be influenced by the uniformity (or lack thereof) of the culturing environment include local cell number and concentration of extracellular matrix components as well as thickness of the tissue construct. Culturing environment parameters which may influence these end properties include local soluble nutrient concentration (including carbon, nitrogen, and oxygen sources), temperature, and pH level.

The culturing environment parameters may be controlled by manipulating the flow of the fluid culturing medium.

Although culture of tissue in a stagnant environment is possible, in a preferred embodiment, the culturing medium is continuously or intermittently perfused across the surface of the tissue construct. So as to maintain a uniform pH level, temperature, and gas concentration across the construct, it is important that a uniform flow profile across the surface of the construct be created.

Maintenance of an adequately uniform flow profile (local velocities withing approximately 25–100% of the mean velocity) is an important design consideration for the culture of a tissue withing relatively uniform properties across all areas of the mesh. This may be achieved in the cassette, as illustrated by the internal views of cassette 300 shown in FIGS. 11A–11B, through a combination of deflector plates 700 and 705, fluid distribution channels 710 and 730, and a flow channel 720.

In accordance with the present invention, during culturing, the cassette 300 is preferably placed in a vertical position with inlet port 340 proximate to the bottom of the casing and outlet port 350 proximate to the top of the casing. The vertical position allows bubbles formed during tissue processing to be vented out the top of the chamber and thus eliminates the formation of bubbles that may occlude tissue growth.

Fluid may be pumped into inlet port 340 and cassette 300 by any standard pumping mechanism that is compatible with closed-circuit operation for maintenance of asepsis. Once the fluid enters cassette 300 through port 340, it enters the inlet fluid distribution channel 710. As shown in FIG. 11B, the depth (measured from arrow A to arrow B) of fluid distribution channels 710 and 730 is preferably greater than the depth (measured from arrow C to arrow D) of the fluid flow channel. The greater depth of the distribution channels is advantageous in that it promotes even distribution of fluid from a point delivery source (inlet port 340) across the entire surface of the tissue construct. Although a flow distributor such as distribution channel 710 is preferred, other passive distributor designs, such as a pressure restrictor plate, may be utilized to provide adequate uniformity of flow and cell seeding efficiency. Cell seeding efficiency is proportional to the hold-up volume in the system. Thus, it is desirable to minimize the hold-up volume in areas of the growth chamber not containing tissue scaffolds.

Deflector plate 700 further ensures an adequately uniform flow profile by spreading out fluid from the inlet port across the complete width of the cassette. Deflector plate 705 is advantageous in that it directs any bubbles in the cassette through the outlet port. The optimum angle of deflector plates 700 and 705 relative to the flow direction is dependant upon the actual flow rate used during growth of the tissue.

In this manner, it is ensured that fluid flow from inlet distribution channel 710 uniformly travels through fluid flow channel 720, and thus scaffold 400 located in said channel. Once the fluid has crossed flow channel 720, it enters exit distribution channel 730 and exits outlet 350. In this manner, a uniform environment for the culturing of tissue scaffolding is provided.

The design parameters which must be considered to ensure adequately uniform fluid flow include the diameter of the inlet orifice, angle of the deflector plates, and ratio of the distribution channel depth to the flow channel depth. Although one skilled in the art will understand that a variety of physical parameters are acceptable in conjunction with the disclosed structure, one exemplary system includes inlet ports having a diameter of approximately 0.10 to 0.16", a flow rate of approximately 30 to 140 ml/minute, a deflector plate angle of approximately 2 to 6 degrees, and a ratio of distribution to flow channel depth approximately greater than or equal to two (e.g., ¼" distributor depth and ⅛" channel depth).

As is the case with the first embodiment of the invention, once the tissue culture has reached the desired level of cell density within cassette 300, the growth medium is removed and the product is rinsed with a phosphate buffered saline solution. After completion of the rinse step, the growth chamber is filled through ports 340 and 350 with freezing solution consisting of a physiological pH buffering system, such as PBS or HEPES, which optionally may be also be supplemented with one or more cyroprotectants such as DMSO, and ancillary agents such as FBS. Once the growth chamber is filled with the preservative solution, the inlet and outlet ports may be sealed in a manner discussed previously, such as by heat sealing, so as to be used to store and/or ship the cultured and preserved tissue construct in an aseptic manner. The individual chambers may then be inspected, labeled, outer protective covering added, and frozen also in the manner described previously.

Frozen cassettes 300 may then be sent to users with the tissue scaffold sealed inside the cassette. When a tissue scaffold is desired to be used, it is first thawed by, for example, placing it in a warm temperature or warm water bath. Ports 340 and 350 provided on the ends of the chamber are attached to tubes and the cryoprotectant is drained. Saline may then be provided to the chamber to rinse the tissue. Once the tissue has been adequately rinsed, it is ready for use by medical personnel. In this manner, cassette 300 may be used to sterilize, culture, store, ship and utilize tissue constructs.

Figure 12:
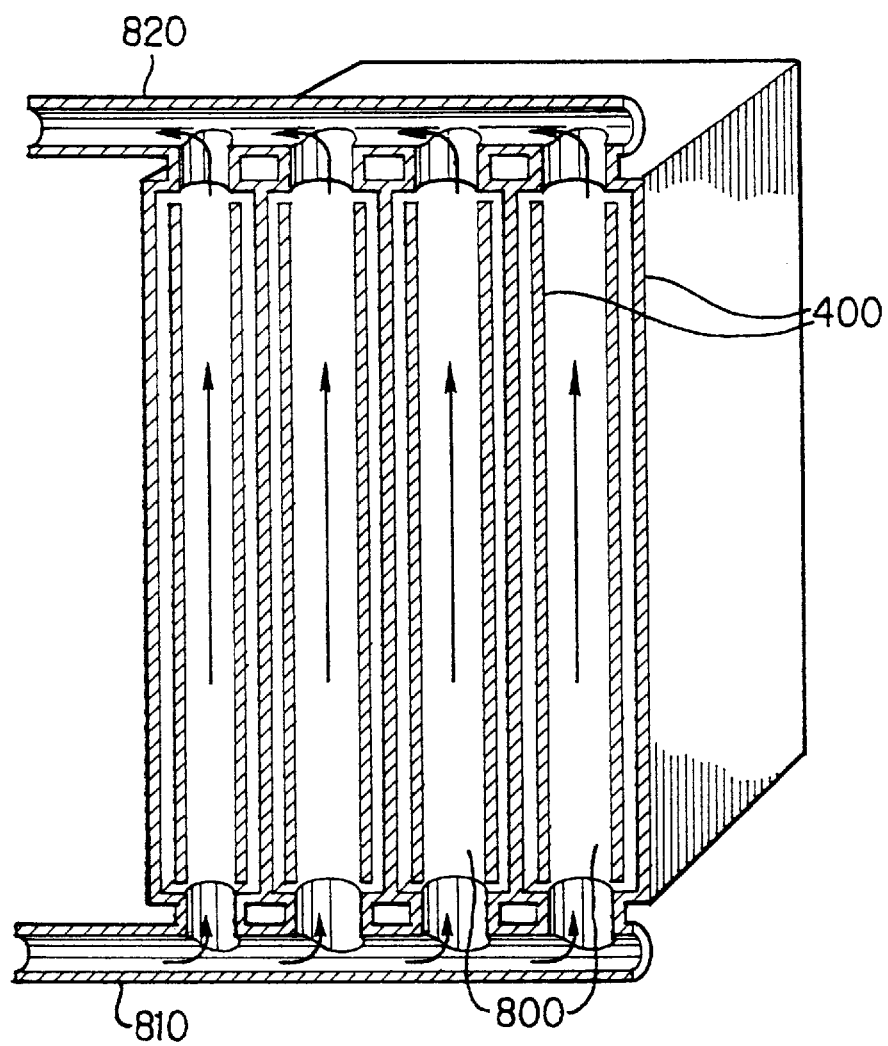
FIG. 12 illustrates an alternative exemplary embodiment of a casing which includes multiple flow channels.

FIG. 12 illustrates yet another alternative embodiment of the present invention. While only one flow channel containing two scaffolds 400 is shown in FIG. 8, as shown in FIG. 12, multiple flow channels may be included in one cassette. In this embodiment, any number of individual chambers 800 may be included together in a cassette such that a number of scaffolds 400 may be cultured at one time.

In this embodiment, optimum processing parameters are scaled up from the single flow channel discussed earlier in relative proportion to the number of flow channels used in the cassette. For example, sufficient fluid flow should be provided to the cassette to enable a flow rate of approximately 30 to 140 ml/min to each flow channel within the cassette.

Figure 13C:
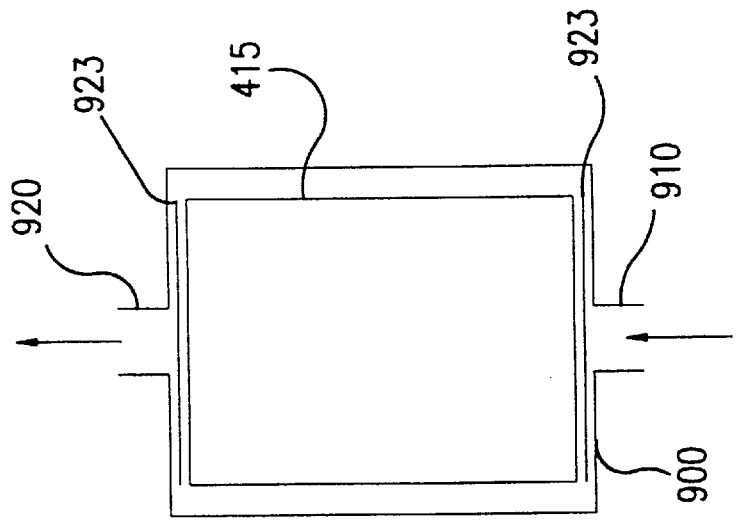
FIGS. 13A–13C illustrate yet another alternative exemplary embodiment of a casing, wherein FIG. 13A discloses a tissue scaffold and a scaffold backing, FIG. 13B discloses an end view of a rolled tissue scaffold and backing, and FIG. 13C discloses a cylindrical cassette including the rolled scaffold.
Figure 13B:
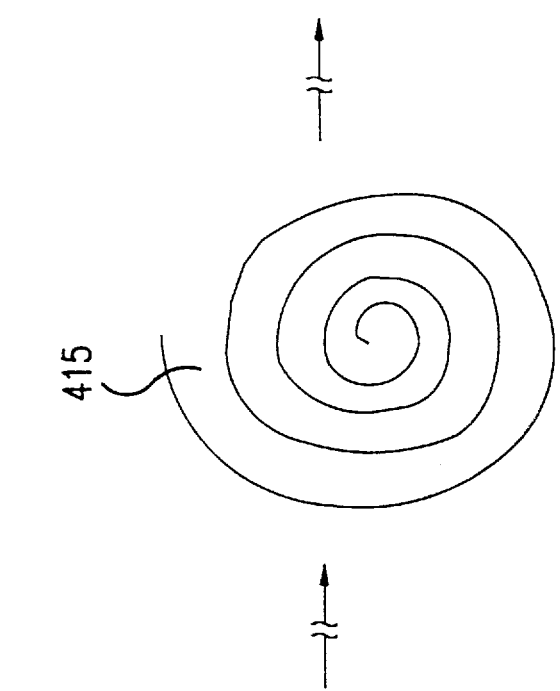
Figure 13A:
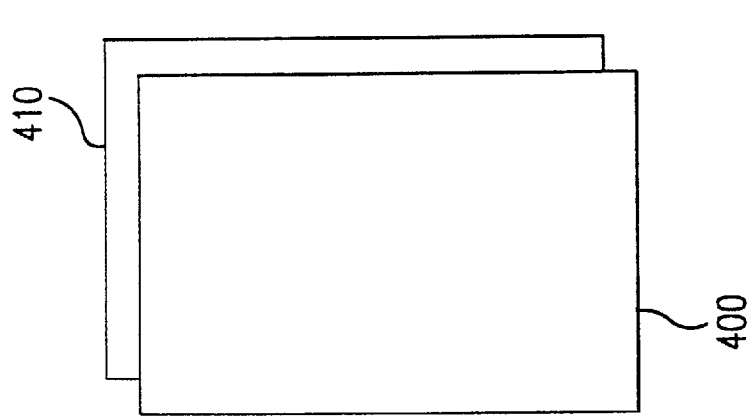
Figure 14A:
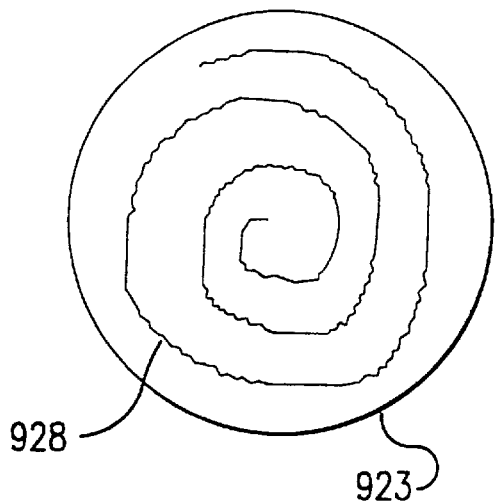
Figure 14B:
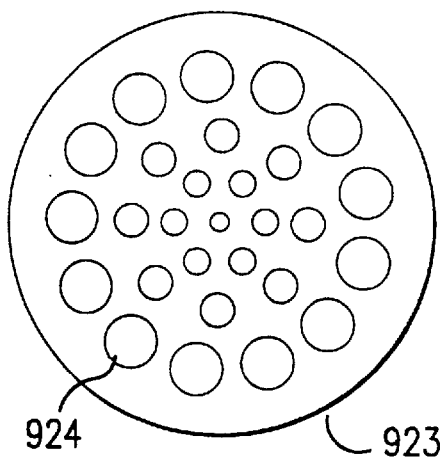
Figure 14C:
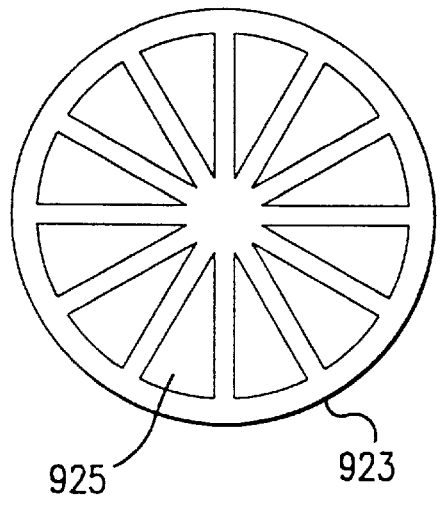
Figure 14D:
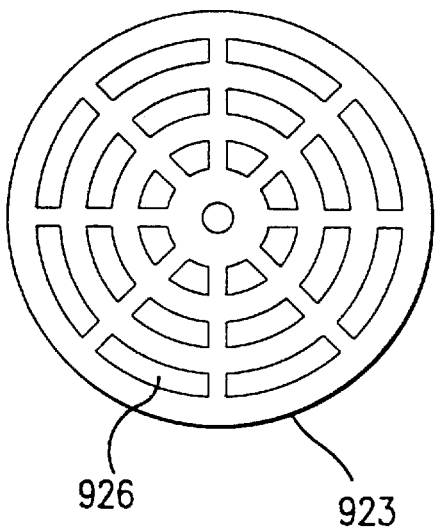
Figure 14E:
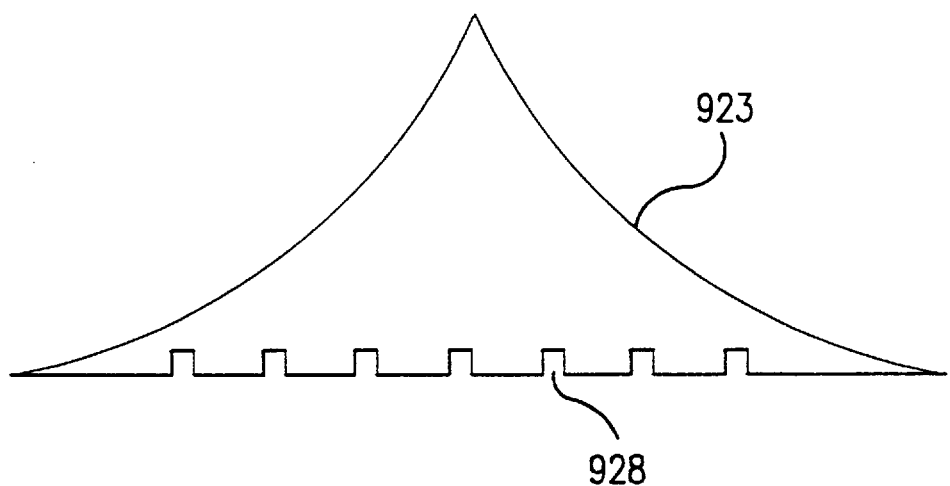
Figure 14F:
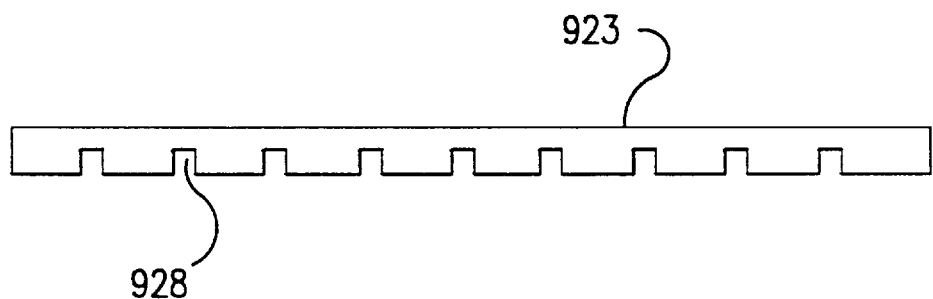

FIGS. 13A–13C disclose yet another alternative embodiment of a growth chamber, in which the culture of larger pieces of tissue may be facilitated. In this embodiment, scaffold 400 is rolled up along with a scaffold backing 410 so as to form a spiral-shaped scaffold 415 prior to insertion into a cylindrically shaped body 900. Body 900 includes an inlet port 910 and an outlet port 920. As with earlier discussed embodiments, body 900 should be maintained in a vertical orientation during culturing so that inlet port 910 is proximate to the bottom of the body and outlet port 920 is proximate to the top. Body 900 also contains endplates 923 at its inlet and outlet for even distribution of fluid through scaffold 415. These endplates 923 may be attached to the body 900 and scaffold 415 such that the spacing between spiral winds is supported and maintained in a spiral groove 928 (shown in FIG. 14A) which may be included on plates 923. Apart from spiral groove 928, plates 923 may be configured in any manner so as to cause even fluid flow and distribution across scaffold 415. FIGS. 14B–14D disclose alternative embodiments of endplates 923. In FIG. 14B, the endplates include perforations 924 with smaller holes near the center and larger holes near the sides. In FIG. 14C, the endplates include slotted perforations 925 which increase in size as they extend to the outer edge of the endplate. In FIG. 14D, the endplates include slit-shaped perforations 926 in a circular pattern which increase in size as they extend to the outer edge of the endplate. Endplates 923 may also be varied in shape depending on the flow distribution required in a particular embodiment. For example, in FIG. 14E, the endplates are conical in shape so as to encourage even fluid distribution, while in FIG. 14F, the endplates are formed in the shape of a plate (although not shown in FIGS. 14E and 14F, the endplates must always have some type of perforation as explained above for even fluid flow and distribution). Although these various endplate embodiments are described particularly, one skilled in the art will understand that many other endplate or baffle configurations may be used with the cylindrical body 900, and which would fall with in the scope of the present invention. All that is necessary is that growth media fluid be supplied and that the endplates be configured in a manner which enables fluid to be simultaneously and evenly distributed to all of the winds of the scaffold spirals.

Various embodiments of the invention have been described. The descriptions are intended to be illustrative, not limitative. Thus, it will be apparent to those skilled in the art that modifications may be made to the invention as described without departing from the scope of the claims set out below.

What is claimed is:

1. An apparatus for three-dimensional tissue growth comprising:
    a casing with an inner and outer surface;
    a substrate disposed within said casing designed to facilitate three-dimensional tissue growth on said substrate;
    an inlet port for the inflow of media into said casing;
    an outlet port for the outflow of media from said casing; and
    means for evenly distributing media flow across and generally parallel to the substrate as it flows from the inlet port to the outlet port, said means disposed within said casing and comprising at least one fluid flow channel having a predetermined width, depth, and height and at least one fluid distribution channel communicating with the fluid flow channel, said fluid distribution channel disposed proximate to said inlet port and having a depth greater than the depth of the fluid flow channel such that media flowing from the inlet port first accumulates in the distribution channel to facilitate even distribution of fluid across the flow channel.

2. The apparatus of claim 1, wherein said distribution channel is defined by at least one deflector plate, said deflector plate disposed within said casing and configured to distribute media from the inlet port.

3. The apparatus of claim 1, wherein said substrate is comprised of a biocompatible membrane.

4. The apparatus of claim 1, wherein said substrate covers greater than 75% of the inner surface of said casing which is exposed to fluid.

5. The apparatus of claim 1, further comprising at least one tab disposed within and removeably attached to said casing for easy removal of said substrate from said casing.

6. The apparatus of claim 1, further comprising a thumb-strap disposed on the outer surface of said casing for easy handling of said casing.

7. The apparatus of claim 1, wherein said casing further includes a front portion and a back portion and wherein said apparatus further comprises a closure system for sealing together the front portion and back portion of said casing.

8. The apparatus of claim 7, wherein said closure system comprises a retaining band sealingly engaging said front and back portions of said casing.

9. The apparatus of claim 1, wherein said substrate comprises a three-dimensional framework having interstitial spaces bridgeable by cells.

10. The apparatus of claim 9, further comprising a three-dimensional tissue, said tissue comprising a plurality of cells attached to and substantially enveloping said framework.

11. The apparatus of claim 1, wherein said casing defines a growth chamber with spacing sufficient to permit adequate media flow so as to allow for uniform three-dimensional tissue growth.

12. An apparatus for three-dimensional tissue growth, comprising:
    a cassette defining a chamber for culturing tissue;
    a planar substrate disposed within said cassette designed to facilitate three-dimensional tissue growth on said substrate;
    at least one inlet port for the inflow of media into said cassette;
    at least one outlet port for the outflow of media from said cassette; and
    a flow distributor disposed within said cassette for evenly distributing media flow through the cassette and generally parallel to the planar substrate as it flows from the inlet port to the outlet port, said flow distributor comprising a first and a second fluid distribution channel and a fluid flow channel;
    said fluid flow channel having a predetermined width, depth, and height;
    said first fluid distribution channel disposed proximate to said inlet port and communicating with the fluid flow channel, said first fluid distribution channel having a depth greater than the depth of the fluid flow channel such that media flowing from the inlet port first accumulates in the distribution channel to facilitate even distribution of fluid across the flow channel; and
    said second fluid distribution channel disposed proximate to said outlet port and communicating with the fluid flow channel.

13. The apparatus of claim 12, wherein said first distribution channel is defined by at least one deflector plate, said deflector plate disposed within said cassette to distribute media from the inlet port.

14. The apparatus of claim 13, wherein said at least one deflector plate is placed at an angle of approximately 2 to 5 degrees with respect to said inlet port.

15. The apparatus of claim 12, wherein said first and second distribution channels have a depth greater than said flow channel.

16. The apparatus of claim 15, wherein said distribution channel depth and said flow channel depth have a ratio greater than or equal to about two.

17. The apparatus of claim 12, wherein said cassette further includes a front portion and a back portion connected by at least one hinge, and wherein said apparatus further comprises a latch disposed on said cassette for easy opening and closing of said cassette.

18. The apparatus of claim 12, further comprising a retaining band disposed around said cassette for aseptically sealing said cassette during use.

19. The apparatus of claim 12, wherein said substrate material is secured into position primarily by electrostatic and hydrophobic forces.

20. The apparatus of claim 19, further comprising at least one tab disposed within and removeably attached to said casing for easy removal of said substrate material from said cassette.

21. An apparatus for three-dimensional tissue growth comprising:
   a cylindrically shaped casing;
   a spiral substrate disposed within said casing designed to facilitate three-dimensional tissue growth on said substrate;
   at least one inlet port for the inflow of media into said casing;
   at least one outlet port for the outflow of media from said casing; and
   a flow distributor disposed within said casing for evenly distributing media across the substrate as the media flows from the inlet port to the outlet port.

22. The apparatus of claim 21, wherein said flow distributor is disposed proximate to said inlet port.

23. The apparatus of claim 21, wherein said flow distributor includes means for maintaining the spiral shape of the substrate within said casing.

24. The apparatus of claim 21, wherein said flow distributor defines a plurality of openings for media passage therethrough.

25. The apparatus of claim 24, wherein said openings increase in area in the direction of the outer edge of the flow distributor.

26. The apparatus of claim 24, wherein the openings proximate the center of the flow distributor are smaller in diameter than the openings proximate the outer edge of the flow distributor.

27. The apparatus of claim 21, wherein said flow distributor is conical in shape.

28. The apparatus of claim 21, wherein said flow distributor is in the form of a plate.

29. An apparatus for three-dimensional tissue growth, comprising:
   a planar substrate designed to facilitate three-dimensional tissue growth on said substrate;
   a housing having opposed inner surfaces for the growth of tissue thereon and defining
      a growth chamber comprising a flow channel therethrough having a predetermined width, depth and height, and
      a fluid distribution channel communicating with the flow channel, said distribution channel having a depth greater than the depth of the flow channel such that fluid first accumulates in the distribution channel to facilitate even distribution of fluid across the flow channel,
      said growth chamber configured and adapted to evenly distribute media flow through the housing and generally parallel to the planar substrate disposed therein;
   an outlet port communicating with the flow channel; and
   an inlet port for introducing fluid into the flow distribution channel.

30. The apparatus according to claim 29, wherein the fluid distribution channel communicates with the flow channel across substantially its entire height.

31. The apparatus according to claim 29, wherein the fluid distribution channel has a bevelled wall such that the height is greater adjacent the inlet port in order to further facilitate even distribution of fluid across the flow channel.

32. The apparatus according to claim 29, wherein the housing is vertically mounted with the inlet port and distribution channel at the bottom such that flow through the flow channel is in an upward direction thereby permitting bubbles to rise to the outlet.

33. The apparatus according to claim 32, wherein the housing further defines an exit distribution channel disposed between the flow channel and the outlet port, said exit distribution channel having a predetermined width, depth and height, with said height being greater adjacent the outlet port to define a bevelled upper edge tending to direct bubbles toward the outlet port.

34. The apparatus according to claim 33, wherein the exit distribution channel communicates with the flow channel across substantially it entire depth.

35. A chamber for three-dimensional tissue growth comprising:
   a casing;
   a substrate disposed within said casing designed to facilitate three-dimensional tissue growth on said substrate;
   at least one inlet port for the inflow of media into said casing;
   at least one outlet port for the outflow of media from said casing; and
   means for evenly distributing media flow across the casing and generally parallel to the substrate as it flows from the inlet port to the outlet port.

36. The chamber of claim 35, wherein said means for distributing flow comprises at least one baffle disposed within said casing to distribute media from the inlet port.

37. The chamber of claim 36, wherein said baffle is disposed proximate to said inlet port.

38. The chamber of claim 37, wherein said baffle has a center portion and two end portions, said center portion having a greater height than said two end portions and positioned directly proximate to said inlet port.

39. The chamber of claim 38, wherein said baffle has an extending block portion located directly in front of said inlet port to distribute the flow of incoming media.

40. The chamber of claim 37, wherein said baffle defines a plurality of holes for fluid passage with the holes increasing in diameter away from the inlet port.

41. The chamber of claim 35, wherein said substrate is made of a biocompatible mesh material.

42. The chamber of claim 35, wherein said substrate comprises a three-dimensional framework having interstitial spaces bridgeable by cells.

43. The chamber of claim 42, further comprising a three-dimensional tissue, said tissue comprising a plurality of cells attached to and substantially enveloping said framework.

44. The chamber of claim 35, wherein said casing defines a growth chamber with spacing sufficient to permit adequate media flow so as to allow for uniform three-dimensional tissue growth.

45. A chamber for three-dimensional tissue growth, comprising:
   a planar substrate designed to facilitate three-dimensional tissue growth on said substrate, said substrate comprising a biocompatible three-dimensional framework having interstitial spaces bridgeable by cells;
   a casing with bottom, top, front, back and side walls defining a growth chamber configured and dimensioned to support the planar substrate parallel to said front and back walls, said casing defining the growth chamber with spacing sufficient to permit three-dimensional tissue growth;
   at least one inlet port disposed proximate to the bottom wall for inflow of media into said growth chamber;

at least one outlet port disposed proximate to the top wall for outflow of media from said growth chamber; and a baffle disposed within said growth chamber and spaced a first predetermined distance from said bottom wall, said baffle being configured to distribute media from the inlet port substantially evenly across the growth chamber and generally parallel to the planar substrate as it flows to the outlet port.

46. The chamber of claim 45, wherein the top wall is positioned above the bottom wall such that flow from the inlet port to the outlet port is in a vertically upward direction such that bubbles entrained in the media are forced to the outlet port and not retained in the growth chamber.

47. The chamber of claim 45, wherein said substrate material is secured into position and spaced a predetermined distance from the front and back walls by members protruding inward from said front and back walls.

48. The chamber of claim 45, wherein the inlet port is disposed in about the center of the bottom wall and the baffle comprises an elongate member extending across the growth chamber between the side walls to defined an increasing area for media passage in the direction of the side walls away from the inlet port.

49. The chamber of claim 48, wherein the baffle has a decreasing height between the front and back walls in the direction of the side walls.

50. The chamber of claim 48, wherein the baffle defines a plurality of openings for media passage therethrough, said openings increasing in area in the direction of the side walls.

51. The chamber of claim 45, wherein the baffle includes a portion extending towards the inlet port to define a second predetermined distance between the bottom wall and the extending portion across from the inlet portion, said second predetermined distance being less than the first predetermined distance such that said extending portion causes distribution of media impinging thereon.

52. The chamber of claim 45, further comprising a second baffle disposed within said growth chamber and spaced a predetermined distance from said top wall, said baffle being configured to further distribute media substantially evenly across the growth chamber as it flows to the outlet port.

53. The chamber of claim 52, wherein the top wall is bevelled in the direction of the outlet port to direct media and entrained bubbles to the outlet port.

54. The chamber of claim 45, including a length of tubing supplying media to the inlet port, wherein the inlet port diameter and tubing diameter are sized to permit free flow of cells in the media therethrough, and wherein the tubing has a length which in combination with the tubing diameter creates a pressure drop of at least about 2.0 inches of water in the media entering the growth chamber.

55. The chamber of claim 45, wherein a seal is provided to maintain an aseptic environment within the chamber during growth of tissue.

56. The chamber of claim 55, wherein said seal is comprised of layers of polyester film.

57. The chamber of claim 55, wherein said chamber further includes an additional inlet port and an additional outlet port.

58. A chamber for three-dimensional tissue growth comprising:

a casing with bottom, top, front, back and side walls defining a growth chamber;

a plurality of pins extending from said front and back walls;

a substrate disposed within said casing designed to facilitate three-dimensional tissue on the surface of said substrate, said pins preventing movement of said substrate within the casing;

an inlet port for the inflow of media proximate to the bottom of said casing;

an outlet port for the outflow of media proximate to the top of said casing;

a first baffle disposed within said casing proximate to said inlet port shaped to distribute media from the inlet port across said casing and generally parallel to said substrate, said baffle including an extending block portion directly proximate to said inlet port; and a second baffle disposed within said casing proximate to said outlet port shaped to distribute media within the casing and generally parallel to said substrate, said baffle including an extending block portion directly proximate to said outlet port.

59. The chamber of claim 58, wherein said first and second baffles each have a center portion and two end portions, said center portion of each said baffle having a greater height than the two end portions of each said baffle.

60. The chamber of claim 58, wherein said back and said front are connected with at least one hinge.

61. The chamber of claim 60, wherein said front further includes a lifting tab to lift said front from said back in cooperation with said at least one hinge.

62. A chamber for three-dimensional tissue growth comprising:

a casing defining a growth chamber of a size sufficient to permit three-dimensional tissue growth;

a substrate disposed within said casing designed to facilitate three-dimensional tissue growth on said substrate, said substrate comprising a three-dimensional framework having interstitial spaces bridgeable by cells;

at least one inlet port for the inflow of media into said casing;

at least one outlet port for the outflow of media from said casing; and means for evenly distributing media flow across the casing and generally parallel to the substrate as it flows from the inlet port to the outlet port.

63. The chamber of claim 62, further comprising a three-dimensional tissue, said tissue comprising a plurality of cells attached to and substantially enveloping said framework.

* * * * *